United States Patent
Jariwala et al.

(10) Patent No.: US 6,288,157 B1
(45) Date of Patent: Sep. 11, 2001

(54) ALKYLATED FLUOROCHEMICAL OLIGOMERS AND USE THEREOF

(75) Inventors: Chetan P. Jariwala, Woodbury; Thomas P. Klun, Lakeland, both of MN (US); Rudolf J. Dams, Antwerp (BE); Marvin E. Jones, Grant, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 09/309,836

(22) Filed: May 11, 1999

(51) Int. Cl.$^7$ ........................................ C08K 3/00
(52) U.S. Cl. .................. 524/462; 524/463; 526/242; 526/250; 526/253; 526/254; 526/255
(58) Field of Search .................... 526/242, 250, 526/253, 254, 255; 524/462, 463

(56) References Cited

U.S. PATENT DOCUMENTS

| | | | |
|---|---|---|---|
| Re. 30,782 | 10/1981 | van Turnhout | 264/22 |
| Re. 31,285 | 6/1983 | van Turnhout et al. | 55/155 |
| 2,803,615 | 8/1957 | Ahlbrecht et al. | 260/29.6 |
| 2,803,656 | 8/1957 | Ahlbrecht et al. | 260/556 |
| 2,841,573 | 7/1958 | Ahlbrecht et al. | 260/79.3 |
| 3,758,447 | 9/1973 | Falk et al. | 260/78.5 |
| 3,890,271 | 6/1975 | Kokoszka | 260/46.5 |
| 3,899,563 | 8/1975 | Oxenrider et al. | 264/211 |
| 3,960,575 | 6/1976 | Martin | 106/10 |
| 3,971,373 | 7/1976 | Braun | 128/146.2 |
| 4,100,324 | 7/1978 | Anderson et al. | 428/288 |
| 4,302,366 | 11/1981 | Perronin et al. | 252/8.57 |
| 4,375,718 | 3/1983 | Wadsworth et al. | 29/592 |
| 4,429,001 | 1/1984 | Kolpin et al. | 428/283 |
| 4,588,537 | 5/1986 | Klaase et al. | 264/22 |
| 4,592,815 | 6/1986 | Nakao | 204/165 |
| 4,619,976 | 10/1986 | Morris et al. | 525/439 |
| 4,843,134 | 6/1989 | Kotnour et al. | 526/318.4 |
| 5,025,052 | 6/1991 | Crater et al. | 524/104 |
| 5,143,963 | 9/1992 | Sterling et al. | 524/366 |
| 5,145,727 | 9/1992 | Potts et al. | 428/198 |
| 5,149,576 | 9/1992 | Potts et al. | 428/198 |
| 5,292,796 | 3/1994 | Dams et al. | 524/598 |
| 5,300,357 | 4/1994 | Gardiner | 428/224 |
| 5,300,587 | 4/1994 | Mascia et al. | 525/359.3 |
| 5,314,959 | 5/1994 | Rolando et al. | 525/276 |
| 5,336,717 | 8/1994 | Rolando et al. | 525/64 |
| 5,380,778 | 1/1995 | Buckanin | 524/247 |
| 5,411,576 | 5/1995 | Jones et al. | 95/57 |
| 5,420,015 | 5/1995 | Wuerch | 106/162 |
| 5,451,622 | 9/1995 | Boardman et al. | 524/100 |
| 5,453,540 | 9/1995 | Dams et al. | 564/96 |
| 5,459,188 | 10/1995 | Sargent et al. | 524/319 |
| 5,496,507 | 3/1996 | Angadjivand et al. | 264/423 |
| 5,508,330 | 4/1996 | Coughlin et al. | 524/251 |
| 5,536,157 | 7/1996 | Linz | 425/72.2 |
| 5,681,963 | 10/1997 | Liss | 548/455 |
| 5,705,592 | 1/1998 | Sejpka et al. | 528/42 |

FOREIGN PATENT DOCUMENTS

| | | |
|---|---|---|
| 3041160 | 2/1991 | (JP) . |
| 9323956 | 12/1997 | (JP) . |
| WO 92/15732 | 9/1992 | (WO) . |
| WO 97/07272 | 2/1997 | (WO) . |
| WO 97/22576 | 6/1997 | (WO) . |
| WO 97/22659 | 6/1997 | (WO) . |
| WO 97/22660 | 6/1997 | (WO) . |
| WO 98/15598 | 4/1998 | (WO) . |
| WO 98/51723 | 11/1998 | (WO) . |
| WO 98/51724 | 11/1998 | (WO) . |
| WO 98/51725 | 11/1998 | (WO) . |
| WO 98/51726 | 11/1998 | (WO) . |
| WO 98/51727 | 11/1998 | (WO) . |
| WO 99/05345 | 2/1999 | (WO) . |

OTHER PUBLICATIONS

H.C. Fielding, "Organofluorine Chemicals and Their Industrial Applications", R.E. Banks, Ed., Society of Chemical Industry, 1979, pp. 214–234.

Chujo et al., J. Polymer Science, Part A, 1988, 26, 2991.

Van Wente et al., "Manufacture of Super Fine Organic Fibers", Report No. 4364 of the Naval Research Laboratories, May 25, 1954.

C.N. Davies, "The Separation of Airborne Dust and Particles", Institution of Mechanical Engineers, London, Proceedings 1B, 1952.

Van Wente, "Superfine Thermoplastic Fibers", Industrial Engineering Chemistry, vol. 48, 1956, pp. 1342–1346.

Primary Examiner—Edward J. Cain
(74) Attorney, Agent, or Firm—Kent S. Kokko

(57) ABSTRACT

This invention provides fluorochemical compounds comprising: a fluorochemical oligomeric portion comprising an aliphatic backbone with a plurality of pendant fluoroaliphatic groups, each fluoroaliphatic group having a fully fluorinated terminal group and each independently linked to a carbon atom of the aliphatic backbone through an organic linking group; an aliphatic moiety; and a linking group which links the fluorochemical oligomeric portion to the aliphatic moiety. The fluorochemical compounds are useful as topical treatments for fibrous substrates such as textiles and fabrics, and as polymer melt additives to provide desirable oil-, water- and stain repellency to shaped articles such as fibers.

21 Claims, No Drawings

ALKYLATED FLUOROCHEMICAL OLIGOMERS AND USE THEREOF

This invention relates to fluorochemical compositions for use in providing repellent properties to a substrate material. In another aspect, this invention relates to fluorochemical compounds that contain pendent fluoroaliphatic groups proximal to one another. In yet another aspect, it relates to fluorochemical compounds that are at least in part oligomeric in nature. This invention also relates to thermoplastic compositions comprising the fluorochemical composition and shaped articles made from the thermoplastic composition.

The utility of organofluorine compounds as surface-active agents (i.e., surfactants) and surface-treating agents is due in large part to the extremely low free-surface energy of a $C_6$–$C_{12}$ fluorocarbon group, according to H. C. Fielding, "Organofluorine Compounds and Their Applications," R. E. Banks, Ed., Society of Chemical Industry at p. 214 (1979). Generally, the organofluorine substances described above are those which have carbon-bonded fluorine in the form of a monovalent fluoroaliphatic radical such as a perfluoroalkyl group, typically —$C_nF_{2n+1}$ where n is at least 3, the terminal part of which group is trifluoromethyl, —$CF_3$.

U.S. Pat. No. 3,758,447 (Falk et al.) describes polymers that result from free radical polymerization of a monomer in the presence of perfluoroalkyl mercaptans, which act as chain-transfer agents. Mercaptans that contain pairs or triplets of closely-packed perfluoroalkyl groups are said to produce polymers with higher oil repellency levels compared with analogous polymers derived from a mercaptan with just one perfluoroalkyl group or perfluoroalkyl groups that are not closely packed.

U.S. Pat. No. 5,453,540 (Dams et al.) describes fluorochemical compositions for the treatment of textiles comprising: (i) a fluorochemical oligomeric portion comprising an aliphatic backbone with a plurality of fluoroaliphatic groups attached thereto, each fluoroaliphatic group having a fully fluorinated terminal group and each independently linked to a carbon atom of the aliphatic backbone through an organic linking group;(ii) an organic moiety (which can be functional or non-functional, and which is different from the fluorochemical oligomeric portion); (iii) a non-polymeric isocyanate-derived linking group which links the fluorochemical oligomeric portion to the organic moiety; and (iv) a group bonded thereto, which can impart soft hand, stain release, water repellency, or a durable property when the compound is applied to a fibrous substrate.

J. Polymer Science, Part A 1988, 26, 2991 (Chujo et al.) describes a di-carboxyl terminated macromonomer prepared by the free radical co-polymerization of a perfluoroalkyl-ethyl acrylate and methyl methacrylate in the presence of thiomalic acid. Also described is the reaction of such macromonomers with organic dicarboxylic acids and organic diamines in the presence of an appropriate catalyst to afford a copolymer wherein the macromonomer is grafted onto a polyamide chain.

Several patents have taught that the addition of certain fluorochemicals to thermoplastic impart oil and stain repellency to thermoplastic articles such as fibers. For example U.S. Pat. No. 5,025,052 (Crater et al.) describes the use of fluoroaliphatic radical-containing 2-oxazolidinone compounds having a monovalent fluoroaliphatic radical bonded to the 5-position thereof with an organic linking group. The compounds are said to be useful in the surface treatment of fibrous materials, such as textiles and are also useful in preparing fibers, films and molded articles by melt-extrusion or injection molding. U.S. Pat. No. 5,380,778 (Buckanin) describes the use of fluorochemical aminoalcohols in thermoplastic compositions which can be melted and shaped, for example by extrusion or molding, to provide fibers and films having desirable oil- and water-repellency properties. U.S. Pat. No. 5,451,622 (Boardman et al.) describes shaped articles, such as fibers and films, made by melt extruding mixtures of fluorochemical piperazine compounds and a thermoplastic polymer. U.S. Pat. No. 5,411,576 (Jones et al.) describes an oily mist resistant electret filter medium comprising melt-blown electret microfibers and a melt-processible fluorochemical having a melting point of at least about 25° C. and a molecular weight of about 500 to 2500, the fluorochemical being a fluorochemical piperazine, oxazolidinone or perfluorinated alkane having from 15 to 50 carbon atoms. U.S. Pat. No. 5,300,587 (Macia et al.) describes oil-repellent polymeric compositions made by blending a perfluoropolyether and a thermoplastic polymer. U.S. Pat. No. 5,336,717 (Rolando et al.) discloses fluorochemical graft copolymers derived from reacting monomers having termianl olefinic bonds with fluorochemical olefins having fluoroaliphatic groups and polymerizable double bonds.

While these fluorochemical melt additives can in some circumstances impart satisfactory hydrophobicity and/or oleophobicity to thermoplastic resins they typically suffer from poor thermal stability above 300° C., a melt processing temperature often encountered in the industry, and they can also be prohibitively expensive, lending limitations to their commercial utility.

For many years nonwoven fibrous filter webs have been made from polypropylene using melt-blowing apparatus of the type described in Report No. 4364 of the Naval Research Laboratories, published May 25, 1954, entitled "Manufacture of Super Fine Organic Fibers" by Van Wente et al. Such melt-blown microfiber webs continue to be in widespread use for filtering particulate contaminants, e.g., as face masks and as water filters, and for other purposes, e.g., to remove oil from water.

Fibrous filters for removing particulate contaminants from the air are also made from fibrillated polypropylene films. Electret filtration enhancement can be provided by electrostatically charging the film before it is fibrillated. Common polymers such as polyesters, polycarbonates, etc. can be treated to produce highly charged electrets but these charges are usually short-lived especially under humid conditions. The electret structures may be films or sheets which find applications as the electrostatic element in electroacoustic devices such as microphones, headphones and speakers and in dust particle control, high voltage electrostatic generators, electrostatic recorders and other applications.

Fibrous polypropylene electret filters that are currently available, some made from melt-blown polypropylene microfibers and others from fibrillated polypropylene film, can show thermally stable electret filtration enhancement. Unfortunately, fibrous electret filters made of polypropylene, whether melt-blown microfibers or fibrillated film, tend to lose their electret enhanced filtration efficiency faster than desired for some purposes when exposed to oily aerosols. There is a growing awareness of the need to improve the long-term efficiency of air filters in the presence of aerosol oils, especially in respirators. It is known to blend about 1 to 20 weight percent poly(4-methyl-1-pentene) with polypropylene to provide resistance to loss of electret enhanced filtration efficiency on exposure to oily aerosols.

SUMMARY OF THE INVENTION

This invention provides fluorochemical compounds comprising:
(i) a fluorochemical oligomeric portion comprising an aliphatic backbone with a plurality of pendant fluoroaliphatic groups, each fluoroaliphatic group having a fully fluorinated terminal group and each independently linked to a carbon atom of the aliphatic backbone through an organic linking group;
(ii) an aliphatic moiety; and
(iii) a linking group which links the fluorochemical oligomeric portion to the aliphatic moiety.

In another aspect, the present invention provides a fluorochemical composition comprising at least one fluorochemical compound described above.

In another aspect, the present invention provides a synthetic organic polymer composition comprising the alkylated fluorochemical oligomer described above and a thermoplastic or thermoset synthetic organic polymer, such as a polyamide, polyurethane, polyester, epoxide or polyolefin. The thermoplastic composition can be melted and shaped, for example by extrusion or molding, to produce shaped articles, such as fibers or films. Said compounds impart desirable oil- and water repellencies to the surfaces of such shaped articles such as films, sheets, fibers and molded articles. The composition is especially useful in the preparation of nonwoven fabrics used in medical gowns, drapes and masks to provided the necessary repellency to bodily fluids. Films containing fluorochemical oligomeric compounds of this invention are useful, for example, for moisture and/or grease-resistant packaging, release liners, and multilayer constructions.

In another aspect, the present invention provides oily mist resistant electret filter medium comprising polypropylene electret fibers and the alkylated fluorochemical oligomer composition described above as a melt processible additive, said additive having a melting temperature of at least 25 deg. C. Preferably the fibers may be in the form of meltblown microfibers.

In another aspect, the present invention provides a method for filtering particulate material from air containing oily aerosol particles comprising passing said air through electret filter media comprising polypropylene melt blown microfibers and a melt processable fluorochemical additive. The electret filter medium of the present invention have improved electret filtration enhancement and sustain that enhancement upon exposure to oily aerosols. Furthermore, the electret filter media of the present invention maintain functional filtration enhancing charge levels under accelerated aging conditions.

The novel fibrous electret filter media are especially useful as an air filter element of a respirator such as a face mask or for such purposes as heating, ventilation, and air-conditioning. In respirator uses, the novel electret filter media may be in the form of molded or folded half-face masks, replaceable cartridges or canisters, or prefilters. In such uses, an air filter element of the invention is surprisingly effective for removing oily aerosols such as are present in cigarette smoke or in fumes from combustion engines. When used as an air filter medium, such as in a respirator, the electret filter medium has surprisingly better filtration performance than does a comparable electret filter media made of 100% polypropylene fibers.

DETAILED DESCRIPTION

The alkylated fluorochemical oligomers in a composition of the invention generally contain a plurality of pendant fluoroaliphatic groups proximal to one another (e.g., located on alternating carbon atoms of an aliphatic backbone, or occasionally on adjacent carbon atoms), as distinct from isolated fluoroaliphatic groups randomly distributed throughout the compound and also as distinct from fluoroaliphatic groups uniformly located on adjacent carbon atoms.

In other preferred embodiments, the invention provides fluorochemical compositions comprising fluorinated compounds of Formulas I or II $$[(A)_m - L]_n R \quad \text{I}$$
$$(A)_m [L - R]_n \quad \text{II}$$

wherein
m is 1 or 2;
n is 1 to 4 inclusive;
each L independently comprises a linking group;
R is a saturated or unsaturated aliphatic moiety of 1 to 75 carbon atoms; and
A is a fluorochemical oligomeric portion of the formula:

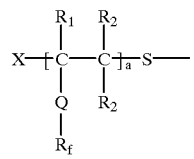

wherein
a is an number such that A is oligomeric and comprises a plurality of pendant $R_f$ groups;
$R_1$ is hydrogen, halogen, or straight chain or branched chain alkyl containing 1 to about 4 carbon atoms;
each $R_2$ is independently hydrogen or straight chain or branched chain alkyl containing 1 to about 4 carbon atoms;
each Q is a covalent bond or an organic linking group, such as a sulfonamidoalkylene group;
$R_f$ is a fluoroaliphatic group, such as —$(CF_2)_7CF_3$, that comprises a fully fluorinated terminal group;
X is a hydrogen atom or a group derived from a free radical initiator (e.g. t-butoxy).

Preferably, with reference to Formulas I and II, both m and n are one to produce an alkylated oligomeric fluorochemical of the Formula IV:

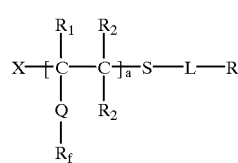

As described above and further illustrated in Formulas I–IV, a fluorochemical composition of the invention comprises an alkylated fluorochemical oligomeric compound that generally has three principal portions: a fluorochemical oligomeric portion "A", a linking group "L", and an aliphatic moiety "R". The fluorochemical oligomeric portion and the organic moiety are linked together by linking group L. The linking group may be a covalent bond, may result from a condensation reaction between a nucleophile, such as an alcohol, an amine, or a thiol, and an electrophile such as a carboxylic acid, ester, acyl halide, sulfonate ester, sulfonyl halide, cyanate, isocyanate, or may result from a nucleophilic displacement reaction between a nucleophile, such as previously described, and a moiety bearing a leaving group, such as the reaction between an alcohol (or alkoxide) and an alkyl halide (where the halogen atom of the alkyl halide serves as a leaving group).

Examples of suitable linking groups L include a covalent bond, straight chain, branched chain, or cyclic alkylene, arylene, aralkylene, oxy, oxo, hydroxy, thio, sulfonyl, sulfoxy, amino, imino, sulfonamido, carboxamido, carbonyloxy, urethanylene, ureylene, and combinations thereof such as sulfonamidoalkylene.

A salient component of the fluorochemical oligomeric portion is the fluoroaliphatic group, designated herein as $R_f$. The fluorinated compound of the invention contains a plurality of pendent $R_f$ groups (e.g., from 2 to about 10) proximal to one another and preferably contains from about 5 percent to about 80 percent, more preferably from about 20 percent to about 65 percent, and most preferably about 25 percent to about 55 percent fluorine by weight, based on the total weight of the compound, the loci of the fluorine being essentially in the $R_f$ groups. $R_f$ is a stable, inert, non-polar, preferably saturated, monovalent moiety which is both oleophobic and hydrophobic. $R_f$ preferably contains at least about 3 carbon atoms, more preferably 3 to about 20 carbon atoms, and most preferably about 4 to about 14 carbon atoms. $R_f$ can contain straight chain, branched chain, or cyclic fluorinated alkylene groups or combinations thereof or combinations thereof with straight chain, branched chain, or cyclic alkylene groups. $R_f$ is preferably free of polymerizable olefinic unsaturation and can optionally contain catenary heteroatoms such as divalent oxygen, or trivalent nitrogen. It is preferred that $R_f$ contain about 35% to about 78% fluorine by weight, more preferably about 40% to about 78% fluorine by weight. The terminal portion of the $R_f$ group contains a fully fluorinated terminal group. This terminal group preferably contains at least 7 fluorine atoms, e.g., $CF_3CF_2CF_2$—, $(CF_3)_2CF$—, or the like. Perfluorinated aliphatic groups (i.e., those of the formula $C_oF_{2o+1}$, where o is 4 to 14 are the most preferred embodiments of $R_f$.

The aliphatic backbone of the fluorochemical oligomeric portion comprises a sufficient number of polymerized units to render the portion oligomeric. The aliphatic backbone preferably comprises from 2 to about 10 polymerized units ("a" in Formula IV) derived from fluorinated monomers (i.e., monomers containing a fluorinated organic group $R_f$ as defined above), it is more preferred that the aliphatic backbone comprise from 3 to about 8, most preferably about 4, polymerized units.

The fluorochemical compositions of the invention generally comprise mixtures of alkylated fluorochemical oligomeric compounds. Accordingly, compounds are sometimes referred to herein as having non-integral numbers of particular substituents (e.g., "a=2.7"). In such cases the number indicates an average and is not intended to denote fractional incorporation of a substituent. The terms "oligomer" or "oligomeric" when used herein designate compounds containing a plurality of polymerized units, but fewer than that number of polymerized units present in a polymer (e.g., chains of 2 to about 10 polymerized units are to be considered "oligomeric").

The fluoroaliphatic group $R_f$ is linked to the organic portion (i.e. the oligomeric backbone or the unsaturated portion of the monomer) by a linking group designated as Q in the formulas used herein. Q is a linking group that is a covalent bond, divalent alkylene, or a group that can result from the condensation reaction of a nucleophile such as an alcohol, an amine, or a thiol with an electrophile, such as an ester, acid halide, isocyanate, sulfonyl halide, sulfonyl ester, or may result from a displacement reaction between a nucleophile and leaving group. Each Q is independently chosen, preferably contains from 1 to about 20 carbon atoms and can optionally contain catenary oxygen, nitrogen, sulfur, or silicon-containing groups or a combination thereof. Q is preferably free of functional groups that substantially interfere with free-radical oligomerization (e.g., polymerizable olefinic double bonds, thiols, easily abstracted hydrogen atoms such as cumyl hydrogens, and other such functionality known to those skilled in the art). Examples of suitable linking groups Q include straight chain, branched chain, or cyclic alkylene, arylene, aralkylene; oxy, oxo, hydroxy, thio, sulfonyl, sulfoxy, amino, imino, sulfonamido, carboxamido, carbonyloxy, urethanylene, ureylene, and combinations and multiples thereof such as sulfonamidoalkylene or polyoxyalkylene. Preferably linking group Q is a covalent bond or a sulfonamidoalkylene group.

Suitable linking groups Q include the following structures in addition to a covalent bond. For the purposes of this list, each k is independently an integer from 0 to about 20, $R_1'$ is hydrogen, phenyl, or alkyl of 1 to about 4 carbon atoms, and $R_2'$ is alkyl of 1 to about 20 carbon atoms. Each structure is non-directional, i.e. —$(CH_2)_kC(O)O$— is equivalent to —$O(O)C(CH_2)_k$—.

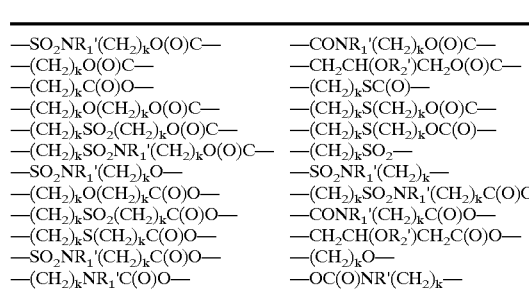

| | |
|---|---|
| —$SO_2NR_1'(CH_2)_kO(O)C$— | —$CONR_1'(CH_2)_kO(O)C$— |
| —$(CH_2)_kO(O)C$— | —$CH_2CH(OR_2')CH_2O(O)C$— |
| —$(CH_2)_kC(O)O$— | —$(CH_2)_kSC(O)$— |
| —$(CH_2)_kO(CH_2)_kO(O)C$— | —$(CH_2)_kS(CH_2)_kO(O)C$— |
| —$(CH_2)_kSO_2(CH_2)_kO(O)C$— | —$(CH_2)_kS(CH_2)_kOC(O)$— |
| —$(CH_2)_kSO_2NR_1'(CH_2)_kO(O)C$— | —$(CH_2)_kSO_2$— |
| —$SO_2NR_1'(CH_2)_kO$— | —$SO_2NR_1'(CH_2)_k$— |
| —$(CH_2)_kO(CH_2)_kC(O)O$— | —$(CH_2)_kSO_2NR_1'(CH_2)_kC(O)O$— |
| —$(CH_2)_kSO_2(CH_2)_kC(O)O$— | —$CONR_1'(CH_2)_kC(O)O$— |
| —$(CH_2)_kS(CH_2)_kC(O)O$— | —$CH_2CH(OR_2')CH_2C(O)O$— |
| —$SO_2NR_1'(CH_2)_kC(O)O$— | —$(CH_2)_kO$— |
| —$(CH_2)_kNR_1'C(O)O$— | —$OC(O)NR'(CH_2)_k$— |

The organic aliphatic moiety, designated R in compounds of Formulas I–IV is a mono-, di-, tri- or tetravalent, linear or branched chain, saturated or unsaturated, cyclic or acyclic (or any combination thereof) organic aliphatic group having from 1 to 75 carbon atoms. In certain embodiments R may be fluorinated (i.e. $R=R_f$). The valency is equivalent to the value of n in Formula I and is equal to 1 in Formula II. The range of structures contemplated for the organic moiety R will be better understood with reference to the compounds suitable for use in steps of the Reaction Schemes described in detail below. Preferably R is a linear, monovalent alkyl group having from 1 to 75 carbon atoms, preferably 12 to 75 carbon atoms, and most preferably 18 to 60 carbon atoms. Where more than one R group is present, such as in Formula II, or when n is greater than one in Formula I, the sum of the carbon atoms in the R groups is preferably 100 carbon atoms or fewer.

The fluorinated compounds and fluorochemical compositions of the invention will be illustrated with reference to the embodiments shown in Formulas I–IV. In such embodiments, linking group L links the fluorochemical oligomeric portion A to the aliphatic group R. Each linking group L may be a covalent bond, a di- or polyvalent alkylene group, or a group that can result from the condensation reaction of a nucleophile such as an alcohol, an amine, or a thiol with an electrophile, such as an ester, acid halide, isocyanate, sulfonyl halide, sulfonyl ester, or may result from a displacement reaction between a nucleophile and leaving group. Each L is independently chosen, preferably contains from 1 to about 20 carbon atoms and can optionally contain catenary (i.e. in-chain) oxygen, nitrogen, sulfur, or silicon-containing groups or a combination thereof. L is preferably free of functional groups that substantially interfere with free-radical oligomerization (e.g., polymerizable olefinic double bonds, thiols, easily abstracted hydrogen atoms such as cumyl hydrogens, and other such detrimental functionalities known to those skilled in the art). Examples of suitable linking groups L include straight chain, branched chain, or cyclic alkylene, arylene, aralkylene, oxy, oxo, sulfonyl, sulfoxy, amino, imino, sulfonamido, carboxamido, carbonyloxy, urethanylene, ureylene, and combinations thereof such as sulfonamidoalkylene. Preferred L groups include the following structures (including combinations and multiples thereof) wherein each k is independently an integer from 0 to about 20, $R_2'$ is alkyl of 1 to about 20 carbon atoms.

| | |
|---|---|
| —(CH$_2$)$_k$O(O)C— | —CH$_2$CH(OR$_2$')CH$_2$C(O)O— |
| —(CH$_2$)$_k$C(O)O— | —(CH$_2$)$_k$O— and |
| —(CH$_2$)$_k$O(CH$_2$)$_k$O(O)C— | |

Returning now to Formulas I–IV above, $R_1$ is hydrogen, halogen (e.g., fluoro, chloro, bromo), or straight chain or branched chain alkyl of 1 to about 4 carbon atoms (e.g., methyl, ethyl, propyl, isopropyl, butyl, isobutyl, and the like). Each $R_2$ is independently hydrogen or straight chain or branched chain alkyl of 1 to about 4 carbon atoms.

X is a group derived from a free-radical initiator. As used herein, the term "free-radical initiator" designates any of the conventional compounds such as organic azo compounds, organic peroxides (e.g., diacyl peroxides, peroxyesters, dialkyl peroxides) and the like that provide initiating radicals upon homolysis. As used herein, the term "group derived from a free-radical initiator" designates an initiating radical formed upon homolytic decomposition of a free-radical initiator.

Suitable groups X include non-reactive groups such as a hydrogen atom, t-butoxy (derived from di-t-butylperoxide), and benzoyloxy (derived from benzoyl peroxide), and reactive groups such as —CCH$_3$(CN)CH$_2$CH$_2$CO$_2$H (derived from azo-4-cyanoisovaleric acid), —C(CH$_3$)$_2$CN (derived from azoisobutyronitrile), and those derived from other known functional azo compounds such as 2,2'-azobis[N-(4-chlorophenyl) -2-methylpropionamidine]-dihydrochloride; 2,2'-azobis[N-(4-hydroxyphenyl) -2-methylpropionamidine]dihydrochloride; 2,2,-azobis[N-(4-aminophenyl) -2-methylpropionamidine]-tetrahydrochloride; 2,2'-azobis[2-methyl -N-2-propenylpropionamidine]dihydrochloride; 2,2'-azobis[N-(2-hydroxyethyl) -2-methylpropionamidine]-dihydrochloride; 2,2'-azobis[2-methyl-N-(2-hydroxyethyl) -propionamide]; 2,2'-azobis[2-(hydroxymethyl)propionitrile]; 2,2'-azobis[2-methyl-N-[1,1-bis(hydroxymethyl)-2-hydroxyethyl] propionamide ]; and 2,2'-azobis{2-methyl-N-[1,1-bis (hydroxymethyl)ethyl]-propionamide}. Preferred groups X include those enumerated above.

The fluorochemical compounds of Formulas I, II and IV can be prepared by oligomerization of an unsaturated, fluorinated compound (V) in the presence of a free-radical initiator and chain-transfer agent of the formula L(SH)$_m$(m= 1–2) according to the following Scheme:

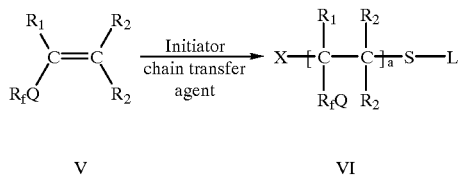

V                  VI

The moiety "L" corresponds to the linking group moiety L of Formula I, II and IV.

When the chain-transfer agent contains more than one sulfhydryl group, multiple fluoroaliphatic groups A may be linked through linking group L to one or more aliphatic R groups. For examples, when the chain transfer agent contains two sulfhydryl groups, two fluoroaliphatic groups A may be linked to L as follows:

Scheme 2

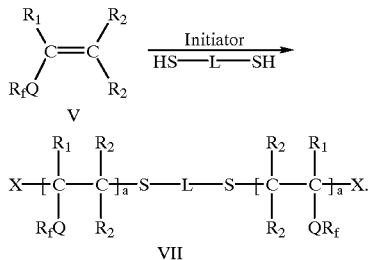

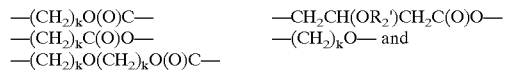

VII

Compounds of Formula (V) and methods for the preparation thereof are known and disclosed, e.g., in U.S. Pat. Nos. 2,803,615 (Ahlbrecht et al.) and 2,841,573 (Ahlbrecht et al.) which disclosures are incorporated herein by reference. Examples of such compounds include general classes of fluorochemical monomers such as acrylates, methacrylates, vinyl ethers, and allyl compounds containing fluorinated sulfonamido groups, acrylates or methacrylates derived from fluorochemical telomer alcohols, fluorochemical thiols, and the like. Preferred compounds of Formula V include N-methyl perfluorooctanesulfonamidoethyl acrylate, N-methyl perfluorooctanesulfonamidoethyl methacrylate, N-ethyl perfluorooctanesulfonamidoethyl acrylate, N-ethyl perfluorohexylsulfonamidoethyl methacrylate, the reaction product of isocyanatoethyl methacrylate and N-methylperfluorooctanesulfonamidoethyl alcohol, 1,1-dihydroperfluorooctyl acrylate, N-methyl perfluorooctanesulfonamidoethyl vinyl ether, $C_8F_{17}SO_2NHCH_2CH=CH_2$, and others such as perfluorocyclohexyl acrylate (c-$C_6F_{11}CH_2OCOCH=CH_2$), and tetrameric hexafluoropropyleneoxide dihydroacrylate.

When the chain transfer agent L(SH)$_m$ bears a functional group, a compound of Formula VI (Scheme I) is further reacted with a functional aliphatic compound to form the linking group L and incorporate the R group into the compounds of Formulas I, II and IV. The nature of the functional groups on both the chain transfer agent and the aliphatic compounds are chosen so that they are reactive toward one another to form the L linking group. Examples of mutually reactive pairs include an acyl group (such as a carboxylic acid, acyl halide or ester) reacting with an alcohol or amine, an alcohol or an amine reacting with a "leaving group" such as a halide or tosylate, and an isocyanate reacting with an alcohol or amine.

A compound of Formulas VI or VII can be provided with functional groups on the L linking group (in addition to the sulfhydryl group(s)) through the use of an appropriate functionalized chain-transfer agent $L(SH)_m$, wherein L contains a functional group. Suitable functional groups for inclusion in the chain-transfer agent include hydroxy, amino, halo, epoxy, haloformyl, aziridinyl, acid groups and salts thereof, which react with an electrophile or nucleophile, or are capable of further transformation into such groups. The use of a functionalized chain-transfer agent allows for subsequent incorporation of the "R" group of Formulas I and II. For example, the "L" group of the chain transfer agent may be substituted with an electrophilic ester moiety. This ester moiety will allow incorporation of a long chain "R" group by further reaction with an aliphatic alcohol having a nucleophilic hydroxyl group. Reaction between the two moieties produces an ester linkage, thereby linking the fluorochemical oligomeric moiety A with the aliphatic moiety R. Alternatively, for example, the L moiety may be substituted with a hydroxyl group that may be reacted with an aliphatic ester to link the fluorochemical oligomeric moiety A with the aliphatic moiety R.

Examples of such functionalized chain transfer agents include 2-mercaptoethanol, mercaptoacetic acid, 2-mercaptobenzimidazole, 2-mercaptobenzoic acid, 2-mercaptobenzothiazole, 2-mercaptobenzoxazole, 3-mercapto-2-butanol, 2-mercaptosulfonic acid, 2-mercaptonicotinic acid, 4-hydroxythiopheno3-mercapto-1,2-propanediol, 1-mercapto-2-propanol, 2-mercaptopropionic acid, N-(2-mercaptopropionyl) glycine, 3-mercaptopropyltrimethoxysilane, 2-mercaptopyridine, 2-mercaptopyridine-N-oxide, 2-mercaptopyridinol, mercaptosuccinic acid, 2,3-mercaptopropanesulfonic acid, 2,3-dimercaptopropanol, 2,3-dimercaptosuccinic acid, cystine, cystine hydrochloride, cystine ethylester. Preferred functionalized chain-transfer agents include 2-mercaptoethanol, 3-mercapto-1,2-propanediol, 4-mercaptobutanol, 11-mercaptoundecanol, mercaptoacetic acid, 3-mercaptopropionic acid, 12-mercaptododecanoic acid, 2-mercaptoethylamine, 1-chloro-6-mercapto-4-oxahexan-2-ol, 2,3-dimercaptosuccinic acid, 2,3-dimercaptopropanol, 3-mercaptopropyltrimethoxysilane, 2-chloroethanethiol, 2-amino-3-mercaptopropionic acid, and compounds such as the adduct of 2-mercaptoethylamine and caprolactam.

Advantageously, the R group of Formulas II, IV and IV may be incorporated by use of a non-functional chain transfer agents. Non-functionalized chain-transfer agents are those that contain a group capable of terminating a radical chain reaction (e.g., a sulfhydryl) but no further functional groups capable of reacting with nucleophiles, electrophiles, or capable of undergoing displacement reactions. In such cases, the aliphatic portion of $L(SH)_n$ provides the aliphatic group R of Formulas I and II. Such compounds include mono, di, and polythiols such as ethanethiol, propanethiol, butanethiol, hexanethiol, n-octylthiol, t-dodecylthiol, 2-mercaptoethyl ether, 2-mercaptoimidazole, 2-mercaptoethylsulfide, 2-mercaptoimidazole, 8-mercaptomenthone, 2,5-dimercapto-1,3,4-thiadiazole, 3,4-toluenedithiol, o-, m-, and p-thiocresol, ethylcyclohexanedithiol, p-menthane-2,9-dithiol, 1,2-ethanedithiol, 2-mercaptopyrimidine, and the like. Longer chain alkyl thiols having 12 to 75 carbon atoms being preferred.

Whether functionalized or not, a chain transfer agent is present in an amount sufficient to control the number of polymerized monomer units in the oligomer. The end-capping agent is generally used in an amount of about 0.05 to about 0.5 equivalents, preferably about 0.25 equivalents, per equivalent of olefinic monomer IV.

Also present in oligomerization process is a free-radical initiator as defined above in connection with X. Such compounds are known to those skilled in the art and include persulfates, azo compounds such as azoisobutyronitrile and azo-2-cyanovaleric acid and the like, hydroperoxides such as cumene, t-butyl, and t-amyl hydroperoxide, dialkyl peroxides such as di-t-butyl and dicumyl peroxide, peroxyesters such as t-butyl perbenzoate and di-t-butylperoxy phthalate, diacylperoxides such as benzoyl peroxide and lauroyl peroxide.

The initiating radical formed by an initiator can be incorporated into the fluorochemical oligomer to varying degrees depending on the type and amount of initiator used. A suitable amount of initiator depends on the particular initiator and other reactants being used. About 0.1 percent to about 5 percent, preferably about 0.1 percent, to about 0.8 percent, and most preferably about 0.2 percent to 0.5 percent by weight of an initiator can be used, based on the total weight of all other reactants in the reaction.

The oligomerization reaction of Schemes 1 and 2 can be carried out in any solvent suitable for organic free-radical reactions. The reactants can be present in the solvent at any suitable concentration, e.g., from about 5 percent to about 90 percent by weight based on the total weight of the reaction mixture. Examples of suitable solvents include aliphatic and alicyclic hydrocarbons (e.g., hexane, heptane, cyclohexane), aromatic solvents (e.g., benzene, toluene, xylene), ethers (e.g., diethylether, glyme, diglyme, diisopropyl ether), esters (e.g., ethyl acetate, butyl acetate), alcohols (e.g., ethanol, isopropyl alcohol), ketones (e.g., acetone, methyl ethyl ketone, methyl isobutyl ketone), sulfoxides (e.g., dimethyl sulfoxide), amides (e.g., N,N-dimethylformamide, N,N-dimethylacetamide), halogenated solvents such as methylchloroform, FREON™ 113, trichloroethylene, $\alpha,\alpha,\alpha$-trifluorotoluene, fluorinated ethers such as $C_4F_9OCH_3$ and the like, and mixtures thereof The oligomerization can be carried out at any temperature suitable for conducting an organic free-radical reaction. Particular temperature and solvents for use can be easily selected by those skilled in the art based on considerations such as the solubility of reagents, the temperature required for the use of a particular initiator, and the like. While it is not practical to enumerate a particular temperature suitable for all initiators and all solvents, generally suitable temperatures are between about 30 deg. C. and about 200 deg. C.

The alkylated fluorochemical oligomeric compounds of the present invention may be used as additives that can provide oil and water repellency to fibers. The fluorochemical additives are melt processible, i.e., suffer substantially no degradation under the melt processing conditions used to form the fibers. The fluorochemical additive preferably has a molecular weight in the range of about 1000 to 10,000, more preferably in the range of about 1500 to 5000. When used in an electret filter medium, the fluorochemical additive is preferably substantially free from mobile polar and/or ionic species, contaminants and impurities which could increase the electrical conductivity or otherwise interfere with the ability of the fibers to accept and hold electrostatic charges.

The present invention provides a synthetic organic polymer composition comprising one or more of the fluorinated compounds of the invention and a melt-processible synthetic organic polymer. The compounds of the invention are useful as polymer melt additives to impart desirable low surface energy properties to the melt-processible polymer. Useful polymers include both thermoplastic and thermoset polymers and include synthetic linear polyamides, e.g., nylon-6 and nylon-66, polyesters, e.g., polyethylene terephthalate, polyurethanes, epoxides, acrylics, polystyrenes and polyolefins, e.g., polyethylene and polypropylene. Thermoplastic polymers such as polyolefins are preferred. The resultant articles, due to the presence of the fluorochemical additive, have improved oil- and water-repellency, low surface energy and a resistance to soiling.

Shaped articles (e.g., fibers, films and molded or extruded articles) of this invention can be made, e.g., by blending or otherwise uniformly mixing the alkylated fluorochemical oligomer and the solid synthetic polymer, for example by intimately mixing the oligomer with pelletized or powdered polymer, and melt extruding the mixture into shaped articles such as pellets, fibers, or films by known methods. The oligomer can be mixed per se with the polymer or can be mixed with the polymer in the form of a "masterbatch" (concentrate) of the oligomer in the polymer. Masterbatches typically contain from about 10% to about 25% by weight of the fluorochemical additive. Also, an organic solution of the oligomer may be mixed with the powdered or pelletized polymer, the mixture dried to remove solvent, then melted and extruded into the desired shaped article. Alternatively, molten oligomer (as a compound(s) or masterbatch) can be injected into a molten polymer stream to form a blend just prior to extrusion into the desired shaped article.

When using thermoset resins, such as epoxy resins, urethanes and acrylates, the alkylated fluorochemical oligomer may be mixed with the resin and cured by application of heat. Preferably such thermoset resins may be processed by reactive extrusion techniques such as are taught in U.S. Pat. Nos. 4,619,976 (Kotnour) and 4,843,134 (Kotnour) the disclosures of which are herein incorporated by reference.

The amount of oligomer in the composition is that amount sufficient to produce a shaped article having a surface with the desired properties of oil and water repellency and/or soiling resistance. Preferably, the amount of oligomer will be that amount which provides from about 100 to 10,000 ppm fluorine, more preferably 200 to 5000 ppm, most preferably 400 to 3000 ppm fluorine, based on the weight of the shaped article.

After melt extrusion of a fiber, film or extruded article, an annealing step may be carried out to enhance oil and water repellency. Annealing apparently allows the fluorochemical oligomer to migrate to the surface of the thermoplastic polymer with a resultant increase in repellency properties, reduced surface energy, improved solvent resistance and improved release properties. The fiber or film is annealed at a temperature and for a time sufficient to increase the amount of fluorochemical oligomer at the surface. Effective time and temperature will bear an inverse relationship to one another and a wide variety of conditions will be suitable. Using nylon, for example, the annealing process can be conducted below the melt temperature at about 150° to 220° C. for a period of about 30 seconds to 5 minutes. In some cases, the presence of moisture during annealing, e.g., by using an autoclave to anneal, can improve the effectiveness of the fluorochemical oligomer. The annealing method may also serve to reduce the amount of oligomer necessary by maximizing fluorine content at the surface of the polymer. The oligomeric compounds of the invention are also useful in the surface treatment of fibrous substrates to impart improved oil and/or water repellency, and soil and/or stain release properties.

Useful fibrous substrates which may be topically treated (surface treated) include natural textiles and fabrics such as cotton or wool and synthetic fabrics or textiles such as polyester or nylon, as well as paper and leather. Topical treatment can be done via immersion, spray, foam, kiss roll and metering. For example, the substrate can be immersed in a dispersion or solution of the fluorochemical oligomer and agitated until it is saturated. The saturated substrate can then be run through a padder/roller to remove excess dispersion, dried in an oven at a relatively low temperature (e.g., 70° C.) for a time sufficient to remove the dispersion medium (e.g. solvents such as those used in the oligomerization reaction), and cured at a temperature and for a time sufficient to provide a cured treated substrate. This curing process can be carried out at temperatures between 40° C. and about 200° C. depending on the particular composition used. In general, a temperature of about 150° C. for a period of about 10 minutes is suitable. The cured treated substrate can be cooled to room temperature and used as desired, e.g., incorporated or fashioned into a garment such as rainwear.

In addition to their use in modifying the properties of fibers, e.g., polypropylene carpet fibers, as described above, the fluorochemical oligomers are also useful as blend additives to thermoplastic polymer melts from which blown microfibers are made for use in making non-woven fabrics having low surface energy, oil and water repellency and/or soiling resistance. The resin, such as polypropylene, used to form the melt blown microfibers should be substantially free from materials such as antistatic agents which could increase the electrical conductivity or otherwise interfere with the ability of the fibers to accept and hold electrostatic charges. When the fluorochemical compounds of the invention are used as additives to melt blown microfibers, the additive is preferably present in amounts of about 0.2 to 10 weight percent, more preferably from 0.5 to 5 weight percent and most preferably 0.5 to 2 weight percent.

As used herein, the terms "fiber" and "fibrous" refer to particulate matter, generally thermoplastic resin, wherein the length to diameter ratio of the particulate matter is greater than or equal to about 10. Fiber diameters may range from about 0.5 micron up to at least 1,000 microns. Each fiber may have a variety of cross-sectional geometries, may be solid or hollow, and may be colored by, e.g., incorporating dye or pigment into the polymer melt prior to extrusion.

The non-woven webs of fibers of thermoplastic olefinic polymer for use in this invention include non-woven webs manufactured by any of the commonly known processes for producing non-woven webs. For example, the fibrous non-woven web can be made by spunbonding techniques or melt-blowing techniques or combinations of the two. Spunbonded fibers are typically small diameter fibers which are formed by extruding molten thermoplastic polymer as filaments from a plurality of fine, usually circular capillaries of a spinneret with the diameter of the extruded fibers being rapidly reduced. Meltblown fibers are typically formed by extruding the molten thermoplastic material through a plurality of fine, usually circular, die capillaries as molten threads or filaments into a high velocity, usually heated gas (e.g. air) stream which attenuates the filaments of molten thermoplastic material to reduce their diameter. Thereafter, the meltblown fibers are carried by the high velocity gas stream and are deposited on a collecting surface to form a web of randomly disbursed meltblown fibers. Any of the non-woven webs may be made from a single type of fiber or two or more fibers which differ in the type of thermoplastic olefinic polymer and/or thickness. Alternatively, sheath-core fibers can be extruded, containing different polymer compositions in each layer or containing the same polymer composition in each layer but employing the more expensive fluorochemical component in the outer sheath layer.

The melt blown polypropylene microfibers useful in the present invention can be prepared as described in Van Wente, A., "Superfine Thermoplastic Fibers," Industrial Engineering Chemistry, vol. 48, pp. 1342–1346 (1956) and in Report No. 4364 of the Naval Research Laboratories, published May 25, 1954, entitled "Manufacture of Super Fine Organic Fibers" by Van Wente et al. or from microfiber webs containing particulate matter such as those disclosed, for example, in U.S. Pat. Nos. 3,971,373 (Braun), 4,100,324 (Anderson) and 4,429,001 (Kolpin et al.), which patents are incorporated herein by reference. Multilayer constructions of nonwoven fabrics enjoy wide industrial and commercial utility and include uses such as fabrics for medical gowns and drapes. The nature of the constituent layers of such multilayer constructions can be varied according to the desired end use characteristics, and can comprise two or more layers of melt-blown and spun-bond webs in may useful combinations such as described in U.S. Pat. Nos. 5,145,727 and 5,149,576, both descriptions of which are incorporated herein by reference. The filtering efficiency of a melt-blown microfiber web can be improved by a factor of two or more when the melt-blown fibers are bombarded as they issue from the orifices with electrically charged particles such as electrons or ions, thus making the fibrous web an electret. Similarly, the web can be made an electret by exposure to a corona after it is collected. Melt-blown polypropylene microfibers are especially useful, while other polymers may also be used such as polycarbonates and polyhalocarbons that may be melt-blown and have appropriate volume-resistivities under expected environmental conditions.

Any of a wide variety of constructions, especially multilayer constructions such as SMS (spunbond/meltblown/spunbond) constructions, may be made from the above-described fibers and fabrics, and such constructions will find utility in any application where some level of hydrophobicity, oleophobicity (or other fluid repellency, such as to bodily fluids) is required. The fibers prepared from the synthetic organic polymer composition of the invention may be used in woven and nonwoven medical fabrics (such as drapes, gowns and masks), industrial apparel, outdoor fabrics (such as umbrellas, awnings, tents, etc), raincoats and other outdoor apparel, as well as home furnishings such as table linens and shower curtains, and in myriad other related uses.

Preferably, the filter media are annealed, i.e. heated for a sufficient time at a sufficient temperature to cause the fluorochemical additive to bloom to the surface of the fibers. Generally, about 1 to 10 minutes at about 140 deg. C. is sufficient although shorter times may be used at higher temperatures and longer times may be required at lower temperatures.

Blown microfibers for fibrous electret filters of the invention typically have an effective fiber diameter of from about 2 to 30 micrometers, preferably from about 7 to 10 micrometers, as calculated according to the method set forth in Davies, C. N., "The Separation of Airborne Dust and Particles," Institution of Mechanical Engineers, London, Proceedings 1B, 1952.

The electret filter medium of the present invention preferably has a basis weight in the range of about 10 to 500 $g/m^2$, more preferably about 10 to 100 $g/m^2$. In making melt-blown microfiber webs, the basis weight can be controlled, for example, by changing either the collector speed or the die throughput. The thickness of the filter media is preferably about 0.25 to 20 mm, more preferably about 0.5 to 2 mm. The electret filter media and the polypropylene resin from which it is produced should not be subjected to any unnecessary treatment which might increase its electrical conductivity, e.g., exposure to gamma rays, ultraviolet irradiation, pyrolysis, oxidation, etc.

The melt-blown microfibers or fibrillated fibers of the electret filters of the invention can be electrostatically charged by a process described in U.S. Pat. Nos. Re. 30,782 (van Turnhout) or Re. 31,285 (van Turnhout) or by other conventional methods for charging or polarizing electrets, e.g., by a process of U.S. Pat. Nos. 4,375,718 (Wadsworth et al.); 4,588,537 (Klasse et al.); or 4,592,815 (Nakao). In general, the charging process involves subjecting the material to corona discharge or pulsed high voltage. Alternatively the fibers may be charged by impinging a jet or stream of water droplets, followed by drying to provide the web with filtration enhancing electret charge as described in U.S. Pat. No. 5,496,507 (Angadjirand et al.)

This invention is illustrated by, but is not intended to be limited to, the following examples.

EXAMPLES

Unless otherwise specified, all percentages shown in the examples and test methods which follow are percentages by weight.

Glossary

TELOMER-A—FLUOWET™ AC-812 fluoroacrylate monomer, $(CH_2=CHC(O)OCH_2CH_2(CF_2)_nCF_3$, where n is a value ranging from about 3 to 11 and averaging about 7, available from Hoechst Aktiengesellschaft, Frankfurt Am Main, Germany).

MeFOSEA—$C_8F_{17}SO_2N(CH_3)C_2H_4OC(O)CH=CH_2$, can be prepared using the general procedure described in U.S. Pat, No. 2,803,615.

EtFOSEA—$C_8F_{17}SO_2N(C_2H_5)C_2H_4OC(O)CH=CH_2$, is available as FLUORAD™ FX-13 fluorochemical acrylate from 3M Company, St. Paul, Minn.

MeFBSEMA—$C_4F_9SO_2N(CH_3)C_2H_4OC(O)C(CH_3)=CH_2$, can be prepared using the general procedure described in U.S. Pat, No. 2,803,615.

MeFBSEA—$C_4F_9SO_2N(CH_3)CH_2CH_2OC(O)CH=CH_2$, can be prepared using the general procedure described in U.S. Pat. No. 2,803,615.

MeFOSEMA—$C_8F_{17}SO_2N(CH_3)C_2H_4OC(O)C(CH_3)=CH_2$, can be prepared by the general procedure described in U.S. Pat. No. 2,803,615.

UNILIN™ 700—polyethylene 700 alcohol (having around 50 carbon atoms), available from Baker Petrolite Corp., Tulsa, Okla.

UNILIN™ 425—polyethylene 460 alcohol (having around 32 carbon atoms), available from Baker Petrolite Corp.

PRIPOL™ 1070—dimer diol made from oleyl alcohol, available from Henkel Corp., Cincinnati, Ohio.

MeFOSE—$C_8F_{17}SO_2N(CH_3)CH_2CH_2OH$, can be prepared using the general procedure described in Example 3 of U.S. Pat. No. 2,803,656.

UNICID™ 700—polyethylene 700 acid (having around 50 carbon atoms), available from Petrolite Corp., St. Louis, Mo.

UNITHOX™ 750—$CH_3CH_2(CH_2CH_2)_xCH_2CH_2(OCH_2CH_2)_yOH$, where x is around 23 and y is around 17, available from Baker Petrolite Corp.

EMPOL™ 1008—distilled and hydrogenated dimer acid made from oleic acid, having an acid equivalent weight of 305 as determined by titration, available from Henkel Corp./Emery Group, Cincinnati, Ohio.

3-mercaptopropionic acid—$HSCH_2CH_2COOH$, available from Aldrich Chemical Co., Milwaukee, Wis.

methyl 3-mercaptopropionate—$HSCH_2CH_2COOCH_3$, available from Aldrich Chemical Co.

2-mercaptoethanol—$HSCH_2CH_2OH$, available from Aldrich Chemical Co.

3-mercapto-1,2-propanediol - $HSCH_2CH(OH)CH_2OH$, available from Aldrich Chemical Co.

AIBN—2,2'-azobisisobutyronitrile, available as VAZO™ 64 initiator from E. I. duPont de Nemours & Co., Wilmington, Del.

FC Oxazolidinone A—a polymer melt additive prepared by reacting $C_8F_{17}SO_2N(CH_3)CH(OH)CH_2Cl$ with stearyl isocyanate at a 1:1 molar ratio followed by ring closure using essentially the same procedure as described in Scheme I of U.S. Pat. No. 5,025,052 (Crater et al.).

FC Oxazolidinone B—a polymer melt additive prepared by reacting $C_8F_{17}SO_2N(Me)CH(OH)CH_2Cl$ with hexamethylene diisocyanate at a 2:1 molar ratio followed by ring closure using essentially the same procedure as described in Scheme I of U.S. Pat. No. 5,025,052 (Crater et al.).

PP3505—Escorene™ PP3505 polypropylene, having a 400 melt index flow rate, available from Exxon Chemical Co., Baytown, Tex.

PP3445—Escorene™ PP3445 polypropylene, having a 35 melt index flow rate, available from Exxon Chemical Co.

PE6806—Aspun™ 6806 polyethylene, having a melt flow index of 105 g/10 min (as measured by Test Method ASTM D-1238) and having a peak melting point of 124.8° C., available from Dow Chemical Co., Midland, Mich.

PS440-200—Morthane™ PS440-200 urethane, available from Morton Thiokol Corp., Chicago, Ill.

Preparation of Compounds and Intermediates (TELOMER-A)$_4$—S—$CH_2CH_2COOH$—To a round bottom flask equipped with stirrer, heating mantle, thermometer, reflux condenser and nitrogen bubbler was added 375 g (0.652 mol) of TELOMER-A and 400 g of ethyl acetate. The contents of the flask were stirred and nitrogen was bubbled through the resulting solution for 15 minutes. To the mixture was then added 17.3 g (0.163 mol) of 3-mercaptopropionic acid, and nitrogen bubbling was continued for another 2 minutes. 0.5 wt % of AIBN was then added, and the resulting catalyzed mixture was heated to 65° C. for approximately 15 hours under a nitrogen atmosphere. IR spectra of this material showed the absence of a>C=C<peak at 1637 $cm^{-1}$, indicating no residual monomer left in the polymer. The polymer solution was poured into hexanes, causing the polymer to precipitate as a white powder, which was removed by filtration and dried under vacuum.

(MeFOSEA)$_4$—S—$CH_2CH_2COOH$—This macromer acid was prepared using essentially the same procedure as described for preparing (TELOMER-A)$_4$—S—$CH_2CH_2COOH$, except that the TELOMER-A was replaced with an equimolar amount of MeFOSEA.

(EtFOSEA)$_4$—S—$CH_2CH_2COOH$—This macromer acid was prepared using essentially the same procedure as described for preparing (TELOMER-A)$_4$—S—$CH_2CH_2COOH$, except that the TELOMER-A was replaced an equimolar amount of EtFOSEA.

(MeFBSEMA)$_4$—S—$CH_2CH_2OH$—To a round bottom flask equipped with stirrer, thermometer, reflux condenser and nitrogen bubbler was added 501 g (1.179 mol) of MeFBSEMA and 500 mL of ethyl acetate. The contents of the flask were stirred to form a solution, and nitrogen was bubbled through the solution for 15 minutes. To this solution was then added 23.03 g (0.295 mol) of 2-mercaptoethanol, and nitrogen was bubbled through the contents of the flask for an additional 2 minutes. 0.5% by weight of AIBN was added and the resulting mixture heated to 65° C. for approximately 15 hours under a nitrogen atmosphere. IR spectra of this material showed the absence of a >C=C<peak at 1637 $cm^{-1}$, indicating no residual monomer present. The polymer solution was poured in hexanes, causing the polymer to precipitate as a viscous liquid, which was removed by decantation and dried under vacuum.

(MeFBSEA)$_4$—S—$CH_2CH_2OH$—This macromer alcohol was prepared using essentially the same procedure as described for preparing (MeFBSEMA)$_4$—S—$CH_2CH_2OH$, except that MeFBSEMA was replaced with an equi molar amount of MeFBSEA.

(MeFOSEA)$_4$—S—$CH_2CH_2OH$—This macromer alcohol was prepared using essentially the same procedure as described for preparing (MeFBSEMA)$_4$—S—$CH_2CH_2OH$, except that MeFBSEMA was replaced with an equimolar amount of MeFOSEA. $^1$H and $^{13}$C NMR analysis showed the degree of polymerization to be slightly greater than 4.

(MeFOSEA)$_9$—S—$CH_2CH_2OH$—This macromer alcohol was prepared using the same procedure as described for preparing (MeFOSEA)$_4$—S—$CH_2CH_2OH$, except that the batch size was scaled up and it is believed that the amount of 2-mercaptoethanol was decreased. In this case, $^1$H and $^{13}$C NMR analysis showed the degree of polymerization to be 9.

(MeFOSEMA)$_4$—S—$CH_2CH_2OH$—This macromer alcohol was prepared using essentially the same procedure as described for preparing (MeFBSEMA)$_4$—S—$CH_2CH_2OH$, except that MeFBSEMA was replaced with an equimolar amount of MeFOSEMA.

(MeFOSEA)$_4$—S—$CH_2CH(OH)CH_2OH$—To a round bottom flask equipped with stirrer, thermometer, reflux condenser and nitrogen bubbler was added 400 g (0.655 mol) of MeFOSEA and 400 mL of ethyl acetate. While stirring, nitrogen was bubbled through the resulting solution for 15 minutes. To this solution was added 17.7 g (0.164 mol) of 3-mercapto-1,2-propanediol, and bubbling with nitrogen was continued for another 2 minutes. 0.5% (wt) of AIBN was added and the mixture was heated to 65° C. for about 15 hours under a nitrogen atmosphere. IR spectra of this material showed the absence of >C=C<peak at 1637 $cm^{-1}$, indicating no residual monomer. This mixture was poured in $CH_3OH$ and the resulting white powder was filtered and dried under vacuum.

(MeFOSEA)$_4$—S—$CH_2CH_2COOCH_3$—To a round bottom equipped with stirrer, thermometer, reflux condenser and nitrogen bubbler was added 200 g (0.327 mol) of MeFOSEA and 200 g of ethyl acetate. The resulting mixture was stirred for 15 minutes, during which time the mixture was bubbled with nitrogen. To the mixture was then added 9.8 g (0.817 mol) of methyl 3-mercaptopropionate, and nitrogen was bubbled through the mixture for an additional two minutes. 0.5% by weight of AIBN initiator was added, and the resulting mixture was heated to 65° C. for about 15 hours under a nitrogen atmosphere. IR spectra analysis of the resulting polymer solution showed an absence of the >C=C<peak at 1637 $cm^{-1}$, indicating essentially no residual monomer. The polymer solution was poured into methanol, causing formation of a white precipitation of the polymer which was removed by filtration and dried under vacuum.

(MeFOSEA)$_4$—S—$CH_2CH_2COO$-UNILIN™ 700—To a 3-necked round bottom flask equipped with a mechanical stirrer and Dean-Stark apparatus was added 50 g (0.0197 mol) of (MeFOSEA)$_4$—S—$CH_2CH_2COOH$, 13.8 g (0.0197 mol) of UNILIN™ 700, 0.5 mL of methanesulfonic acid and 100 mL of toluene. The resulting mixture was heated to reflux for approximately 15 hours, during which time 0.3 mL of water had collected in the Dean-Stark apparatus. IR spectra of this mixture showed no —COOH or —OH peaks. To this hot mixture 10 g of $Ca(OH)_2$ was added slowly with stirring, and the hot solution was filtered. Toluene was removed from the filtrate by heating under reduced pressure, and the remaining solids were dried in a vacuum oven. Differential scanning calorimetry (DSC) analysis of this sample showed a melting transition at 101.4° C., and thermogravimetric analysis (TGA) showed onset of degradation at 330° C. in air.

$(EtFOSEA)_4$—S—$CH_2CH_2$COO-UNILIN™ 700—This ester was prepared using essentially the same procedure as described for preparing $(MeFOSEA)_4$—S—$CH_2CH_2$COO—UNILIN™ 700, except that the $(MeFOSEA)_4$—S—$CH_2CH_2$COOH was replaced with an equimolar amount of $(EtFOSEA)_4$—S—$CH_2CH_2$COOH.

$(TELOMER-A)_4$—S—$CH_2CH_2$COO-UNILIN™ 700— This ester was prepared using essentially the same procedure as described for preparing $(MeFOSEA)_4$—S—$CH_2CH_2$COO-UNILIN™ 700, except that the $(MeFOSEA)_4$—S—$CH_2CH_2$COOH was replaced with an equimolar amount of $(TELOMER-A)_4$—S—$CH_2CH_2$COOH.

$(MeFOSEA)_4$—S—$CH_2CH_2$COO-UNILIN™ 425— This ester was prepared using essentially the same procedure as described for preparing $(MeFOSEA)_4$—S—$CH_2CH_2$COO—UNILIN™ 700, except that the UNILIN™ 700 was replaced with an equimolar amount of UNILIN™ 425.

$(EtFOSEA)_4$—S—$CH_2CH_2$COO-UNILIN™ 425—This ester was prepared using essentially the same procedure as described for preparing $(MeFOSEA)_4$—S—$CH_2CH_2$COO—UNILIN™ 425, except that the $(MeFOSEA)_4$—S—$CH_2CH_2$COOH was replaced with an equimolar amount of $(EtFOSEA)_4$—S—$CH_2CH_2$COOH.

$(TELOMER-A)_4$—S—$CH_2CH_2$COO-UNILIN™ 425— This ester was prepared using essentially the same procedure as described for preparing $(MeFOSEA)_4$—S—$CH_2CH_2$COO-UNILIN™ 425, except that the $(MeFOSEA)_4$—S—$CH_2CH_2$COOH was replaced with an equimolar amount of $(TELOMER-A)_4$—S—$CH_2CH_2$COOH.

$(MeFOSEA)_4$—S—$CH_2CH_2COOC_8H_{37}$—This ester was prepared using essentially the same procedure as described for preparing $(MeFOSEA)_4$—S—$CH_2CH_2$COO—UNILIN™ 700, except that the UNILIN™ 700 was replaced with an equimolar amount of stearyl alcohol.

$(MeFOSEA)_4$—S—$CH_2CH_2COOC_{22}H_{45}$—This ester was prepared using essentially the same procedure as described for preparing $(MeFOSEA)_4$—S—$CH_2CH_2$COO-UNILIN™ 700, except that the UNILIN™ 700 was replaced with an equimolar amount of behenyl alcohol.

$[(MeFOSEA)_4$—S—$CH_2CH_2COO]_2$-PRIPOL™ 1070 —To a 3-necked round bottom flask equipped with a mechanical stirrer and Dean-Stark apparatus was added 50 g (0.0197 mol) of $(MeFOSEA)_4$—S—$CH_2CH_2$COOH, 5.7 g (0.0098 mol) of PRIPOL™ 1070, 0.5 mL of methanesulfonic acid and 100 mL of toluene. The resulting mixture was heated to reflux for approximately 15 hours, during which time 0.3 mL of water had collected in the Dean-Stark apparatus. IR spectra of this mixture showed no —COOH or —OH peaks. To this hot mixture 10 g of $Ca(OH)_2$ was added slowly with stirring, and the hot solution was filtered. Toluene was removed from the filtrate by heating under reduced pressure, and the remaining solids were dried in a vacuum oven.

$(MeFOSEA)_4$—S—$CH_2CH_2COOCH_2CH_2N(CH_3)SO_2C_8F_{17}$—To a 3-necked round bottom flask equipped with a mechanical stirrer and Dean-Stark apparatus was added 50 g (0.0197 mol) of $(MeFOSEA)_4$—S—$CH_2CH_2$COOH, 10.6 g (0.019 mol) of MeFOSE, 0.5 mL of methanesulfonic acid and 100 mL of toluene. The resulting mixture was heated to reflux for approximately 15 hours, during which time 0.3 mL of water had collected in the Dean-Stark apparatus. IR spectra of this mixture showed no —COOH or —OH peaks. To this hot mixture 10 g of $Ca(OH)_2$ was slowly added with stirring, and the hot solution was filtered. Toluene was removed from the filtrate by heating under reduced pressure, and the remaining solids were dried in a vacuum oven.

$(MeFOSEA)_4$—S—$CH_2CH_2$COO-UNITHOX™ 750— This ester was prepared using essentially the same procedure as described for preparing $(MeFOSEA)_4$—S—$CH_2CH_2$COO-UNILIN™ 700, except that the UNILIN™ 700 was replaced with an equimolar amount of UNITHOX™ 750.

$(MeFOSEA)_4$—S—$CH_2CH_2$OOC-UNICID™ 700—To a 3-necked round bottom flask equipped with a mechanical stirrer and Dean-Stark apparatus was added 100 g (0.039 mol) of $(MeFOSEA)_4$—S—$CH_2CH_2$OH, 34.5 g (0.039 mol) of UNICID™ 700, 1.0 mL of methanesulfonic acid and 100 mL of toluene. The resulting mixture was heated to reflux for approximately 15 hours, during which time some water had collected in the Dean-Stark apparatus. IR spectra of this mixture showed no —COOH or —OH peaks. To this hot mixture 10 g of $Ca(OH)_2$ was added slowly with stirring, and the hot solution was filtered. Toluene was removed from the filtrate by heating under reduced pressure, and the remaining solids were dried in a vacuum oven. $^1$H and $^{13}$C NMR analysis showed the degree of polymerization to be 4.2, as calculated from the ratio of the methyl moiety located on the sulfonamido nitrogen to the terminal methyl moiety of the long chain alkyl group.

$(MeFOSEA)_9$—S—$CH_2CH_2$OOC-UNICID™ 700— This ester was prepared using essentially the same procedure as described for preparing $(MeFOSEA)_4$—S—$CH_2CH_2$COO—UNICID™ 700, except that the $(MeFOSEA)_4$—S—$CH_2CH_2$OH was replaced with an equimolar amount of $(MeFOSEA)_9$—S—$CH_2CH_2$OH.

$(MeFOSEMA)_4$—S—$CH_2CH_2$OOC-UNICID™ 700— This ester was prepared using essentially the same procedure as described for preparing $(MeFOSEA)_4$—S—$CH_2CH_2$COO-UNICID™ 700, except that the $(MeFOSEA)_4$—S—$CH_2CH_2$OH was replaced with an equimolar amount of $(MeFOSEMA)_4$—S—$CH_2CH_2$OH.

$(MeFBSEA)_4$—S—$CH_2CH_2$OOC-UNICID™ 700— This ester was prepared using essentially the same procedure as described for preparing $(MeFOSEA)_4$—S—$CH_2$COO—UNILIN™ 700, except that the $(MeFOSEA)_4$—S—$CH_2CH_2CO_2H$ was replaced with an equimolar amount of $(MeFBSEA)_4$—S—$CH_2CH_2$OH and UNILIN™ 700 was replaced with an equimolar amount of UNICID™ 700.

$(MeFBSEMA)_4$—S—$CH_2CH_2$OOC-UNICID™ 700— This ester was prepared using essentially the same procedure as described for preparing $(MeFOSEA)_4$—S—$CH_2CH_2$COO—UNILIN™ 700, except that the $(MeFOSEA)_4$—S—$CH_2CH_2CO_2H$ was replaced with an equimolar amount of $(MeFBSEMA)_4$—S—$CH_2CH_2H$ and UNILIN™ 700 was replaced with an equimolar amount of UNICID™ 700.

$(MeFOSEA)_4$—S—$CH_2CH(OOCC_{17}H_{35})CH_2OOCC_{17}H_{35}$—To a 3-necked round bottom flask equipped with a mechanical stirrer and Dean-Stark apparatus was added 50 g (0.0196 mol) of $(MeFOSEA)_4$—S—$CH_2CH(OH)CH_2OH$, 11.2 g (0.0392 mol) of stearic acid, 0.5 mL of methanesulfonic acid and 100 mL of toluene. The resulting mixture was heated to reflux for approximately 15 hours, during which time some water had collected in the Dean-Stark apparatus. IR spectra of this mixture showed no —COOH or —OH peaks. To this hot mixture 10 g of $Ca(OH)_2$ was added slowly with stirring, and the hot solution was filtered. Toluene was removed from the filtrate by heating under reduced pressure, and the remaining solids were dried in a vacuum oven.

$C_8F_{17}SO_2N(CH_3)CH_2CH_2OOC$-UNICID™ 700—To a 3-necked round bottom flask equipped with a mechanical stirrer and Dean-Stark apparatus was added 135 g (0.242 mol) of MeFOSE, 215.7 g (0.242 mol) of UNICID™ 700, 3.5 g of methanesulfonic acid and 400 mL of toluene. The resulting mixture was heated to reflux for approximately 15 hours, during which time water had collected in the Dean-Stark apparatus. IR spectra of this mixture showed no —COOH or —OH peaks. To this hot mixture 10 g of $Ca(OH)_2$ was added slowly with stirring, and the hot solution was filtered. Toluene was removed from the filtrate by heating under reduced pressure, and the remaining solids were dried in a vacuum oven.

$[C_8F_{17}SO_2N(CH_3)CH_2CH_2OOC]_2$-EMPOL™ 1008—To a 500 mL 2-necked round-bottom flask equipped with overhead condenser, thermometer and Dean-Stark trap wrapped with heat tape was charged 57.8 g (0.190 eq) of Empol™ 1008 dimer acid, 100 g (0.185 eq) of MeFOSE, 1 g of p-toluenesulfonic acid and 50 g of toluene. The resulting mixture was placed in an oil bath heated to 150° C. The degree of esterification was monitored by measuring the amount of water collected in the Dean-Stark trap and also by using gas chromatography to determine the amount of unreacted fluorochemical alcohol. After 18 hours of reaction, about 2.8 mL of water was collected and a negligible amount of fluorochemical alcohol remained, indicating a complete reaction. The reaction mixture was then cooled to 100° C. and was twice washed with 120 g aliquots of deionized water to a water pH of 3. The final wash was removed from the flask by suction, and the reaction mixture was heated to 120° C. at an absolute pressure of about 90 torr to remove volatiles. The product, a brownish solid, was characterized as containing the desired product by $^1H$ and $^{13}C$ NMR spectroscopy and thermogravimetric analysis.

$[(MeFBSEA)_4$—S—$CH_2CH_2OOC]_2$-EMPOL™ 1008— This ester was prepared using essentially the same procedure as described for preparing $C_8F_{17}SO_2N(CH_3)CH_2CH_2OOC]_2$-EMPOL™ 1008, except that the $C_8F_{17}SO_2N(CH_3)CH_2CH_2OH$ was replaced with an equimolar amount of $(MeFBSEA)_4$—S—$CH_2CH_2OH$.

$[(MeFBSEMA)_4$—S—$CH_2CH_2OOC]_2$-EMPOL™ 1008 —This ester was prepared using essentially the same procedure as described for preparing $C_8F_{17}SO_2N(CH_3)CH_2CH_2OOC]_2$-EMPOL™ 1008, except that the $C_8F_{17}SO_2N(CH_3)CH_2CH_2OH$ was replaced with an equimolar amount of $(MeFBSEMA)_4$—S—$CH_2CH_2OH$.

Test Methods

Melt-Blown Extrusion Procedure—The melt-blown extrusion procedure used is the same as described in U.S. Pat. No. 5,300,357, column 10, which is herein incorporated by reference. The extruder used is a Brabender 42 mm conical twin screw extruder, with maximum extrusion temperature of 270–280° C. and distance to the collector of 12 inches (30 cm).

Fluorochemical and thermoplastic polymer mixtures are mixed by blending the thermoplastic polymer and fluorochemical polymer melt additive (if used) in a paperboard container using a mixer head affixed to a hand drill for about one minute until a visually homogeneous mixture is obtained.

The process condition for each mixture is the same, including the melt blowing die construction used to blow the microfiber web, the basis weight of the web (55±5 g/m²) and the diameter of the microfibers (5–18 micrometers). Unless otherwise stated, the extrusion temperature is 270–280° C., the primary air temperature is 210° C., the pressure is 124 kPa (18 psi), with a 0.076 cm air gap width, and the polymer throughput rate is about 180 g/hr/cm.

Film Extrusion Procedure—Films were extruded from Escorene™ PP3445 polypropylene containing either 3% by weight of fluorochemical polymer melt additive or no polymer melt additive using the following procedure. A 25 mm twin screw Bersdorf extruder equipped with a gear pump and slot die having a slot approximately 12 inches (30 cm) wide was fed with Colortronic™ Model CSD (Freidrichsdorf, Germany) dosing units providing 97 wt % polypropylene and 3 wt % of the additive. The extruder was heated so that the extruder and die temperatures were 380° F. (197° C.) and the melt temperature was 401° F. (205° C.). The molten polymer composition was extruded at a rate of about 9 kg/hr onto a casting roll (at 61° C.)to give a film having a thickness of about 7 mil (0.3 mm). The film was allowed to cool before testing.

Water Repellency Test—Nonwoven web samples were evaluated for water repellency using 3M Water Repellency Test V for Floorcoverings (February 1994), available from 3M Company. In this test, samples are challenged to penetrations by blends of deionized water and isopropyl alcohol (IPA). Each blend is assigned a rating number as shown below:

| Water Repellency Rating Number | Blend (% by volume) |
| --- | --- |
| 0 | 100% water |
| 1 | 90/10 water/IPA |
| 2 | 80/20 water/IPA |
| 3 | 70/30 water/IPA |
| 4 | 60/40 water/IPA |
| 5 | 50/50 water/IPA |
| 6 | 40/60 water/IPA |
| 7 | 30/70 water/IPA |
| 8 | 20/80 water/IPA |
| 9 | 10/90 water/IPA |
| 10 | 100% IPA |

In running the Water Repellency Test, a nonwoven web sample is placed on a flat, horizontal surface. Five small drops of water or a water/IPA mixture are gently placed at points at least two inches apart on the sample. If, after observing for ten seconds at a 45° angle, four of the five drops are visible as a sphere or a hemisphere, the nonwoven web sample is deemed to pass the test. The reported water repellency rating corresponds to the highest numbered water or water/IPA mixture for which the nonwoven sample passes the described test.

It is desirable to have a water repellency rating of at least 4, preferably a rating at least 6.

Oil Repellency Test—Nonwoven web samples were evaluated for oil repellency using 3M Oil Repellency Test III (February 1994), available from 3M Company, St. Paul, Minn. In this test, samples are challenged to penetration by oil or oil mixtures of varying surface tensions. Oils and oil mixtures are given a rating corresponding to the following:

| Oil Repellency Rating Number | Oil Composition |
| --- | --- |
| 0 | (fails Kaydol ™ mineral oil) |
| 1 | Kaydol ™ mineral oil |
| 2 | 65/35 (vol) mineral oil/n-hexadecane |
| 3 | n-hexadecane |
| 4 | n-tetradecane |
| 5 | n-dodecane |
| 6 | n-decane |
| 7 | n-octane |
| 8 | n-heptane |

The Oil Repellency Test is run in the same manner as is the Water Repellency Test, with the reported oil repellency rating corresponding to the highest oil or oil mixture for which the nonwoven web sample passes the test.

It is desirable to have an oil repellency rating of at least 1, preferably a rating of at least 3.

DOP Wetting Time Test—Nonwoven webs were challenged to wetting by dioctyl phthalate (DOP) by placing a small drop of neat DOP on the web and measuring the time for the drop to spread or wet the web (considered the time of failure). Webs which were not wet after two days were considered to be resistant indefinitely to DOP.

DOP Penetration and Pressure Drop Test—0.3 micrometer diameter particles of dioctyl phthalate (DOP) at a concentration of between 70 and 110 mg/m$^3$ are generated using a TSI No. 212 sprayer with four orifices and 30 psi (1550 torr) clean air. The particles are forced through the center 4.5 inch (11.4 cm) diameter portion of a circular sample of filter media which is 5.25 inches (13.3 cm) in diameter at a rate of 42.5 L/min, which represents a face velocity of 6.9 centimeters per second. The sample is exposed to the aerosol for 30 to 60 seconds until the readings stabilize. The DOP penetration (% Pn) is measured with an optical scattering chamber (Percent Penetration Meter Model TPA-8F, available from Air Techniques. Inc.). The DOP penetration is preferably less than about 40%, more preferably less than about 30%. The pressure drop is measured at a flow rate of 42.5 L/min and a face velocity of 6.9 cm/sec using an electronic manometer.

Pressure drop, $\Delta P$, is reported in units of millimeters of water. Preferably the pressure drop is less than about 4, more preferably less than about 3.

The penetration and pressure drop are used to calculate a quality value (QF, having units of mm $H_2O^{-1}$) defined by the following formula:

$$QF=-[1n(\%Pn/100)]/\Delta P$$

A higher initial QF value indicates better initial filtration performance. Decreased QF values effectively correlate with decreased filtration performance. Generally a QF value of at least about 0.25 is preferred, a value of at least about 0.4 is more preferred and a value of at least about 0.5 is most preferred.

DOP Loading Test—The same procedure was used as described in the DOP Penetration and Pressure Drop Test with the following modifications. A nonwoven web sample is weighed and then placed in a sample holder which exposed the center 4.5 inch (11.4 cm) diameter portion of the circular sample. A computer is interfaced to record measurements of DOP penetration and pressure drop every minute over a 45 minute period. After this period, the nonwoven sample with collected DOP aerosol is removed, the sample is reweighed, and the penetration is plotted as a function of the DOP weight collected on the web.

Contact Angle Test Procedure—The following procedure was used to measure both advancing and receding contact angles.

A sample of clean polyester film is cut into 85 mm×13 mm rectangular strips. Each strip is cleaned by dipping the strip in and out of methyl alcohol, wiping the strip with a Kimwipe™ wiper (commercially available from Kimberly-Clark Corp., Boswell, Ga.), taking care not to hand-touch the strip's surface, and allowing the strip to dry for 15 minutes. Then, using a small binder clip to hold one end of the strip, the strip is immersed in a treating solution consisting of a 3% (wt) solution of the alkylated fluorochemical oligomer compound in either α,α,α-trifluorotoluene or 50/50 (wt) α,α, α-trifluorotoluene/toluene, and the strip is then withdrawn slowly and smoothly from the solution. The coated film strip is tilted to allow any solution runoff to accumulate at the corner of the strip, and a Kimwipe™ tissue is touched to the corner to pull away the solution buildup. The coated film strip is allowed to air dry in a protected location for a minimum of 30 minutes and then is baked for 10 minutes at 150° C. to dry and cure the coating.

After the treatment is dry and cured, a drop of n-hexadecane is applied to the treated film strip and the advancing or receding contact angle of the drop is measured using a CAHN Dynamic Contact Angle Analyzer, Model DCA 322 (a Wilhelmy balance apparatus equipped with a computer for control and data processing, available from ATI, Madison, Wis.) using the following procedure. The CAHN Dynamic Contact Angle Analyzer is calibrated using a 500 mg weight. An alligator clip is fastened to a piece of coated film strip about 30 mm long, and the clip and film piece are hung from the stirrup of the balance. A 30 mL glass beaker containing approximately 25 mL of n-hexadecane is placed under the balance stirrup, and the beaker is positioned so that the coated film strip is centered over the beaker and its contents but not touching the walls of the beaker. Using the lever on the left side of the apparatus, the platform supporting the beaker is carefully raised until the surface of n-hexadecane is 2–3 mm from the lower edge of the film strip. The door to the apparatus is closed, the "Configure" option is chosen from the "Initialize" menu of the computer, the "Automatic" option is chosen from the "Experiment" menu, and the computer program then calculates the time for a total of 3 scans. The result should be a time interval of 1 second and estimated total time of 5 minutes, which are the acceptable settings to show the baseline weight of the sample. The Return Key is then pressed to begin the automatic measurement cycle. 10 readings of the baseline are taken before the scan begins. The apparatus then raises and lowers the liquid so that 3 scans are taken. The "Least Squares" option is then selected from the "Analysis" menu, and the average advancing or receding contact angle is calculated from the 3 scans of the film sample. The 95% confidence interval for the average of the 3 scans is typically about±1.2°.

Peel Force Test Procedure—Release of pressure-sensitive adhesive tape was measured using a "peel force" test procedure. In this test, a 1.9 cm (0.75 in) wide by 20 cm (8 in) long strip of 3M #850 acrylic adhesive tape was dry-laminated by hand to the melt blended film and was secured with two passes of a 2 kg rubber roller. The peel force to remove the tape from the paper at an angle of 180° and at a peel rate of 229 cm/min (90 in/min) was then measured using an IMASS SP-102B-3M90 peel tester (available from Instrumentors Inc.). Peel force was measured on one sample immediately after preparation ("Initial") and on another sample after aging for two days at 49° C. (120° F.) and ambient humidity using a forced air oven followed by cooling for ½ hour at 50% humidity ("Aged").

Examples 1–19 and Comparative Examples C1–C5

In Examples 1–19, several alkylated fluorochemical oligomeric compounds having an ester moiety-containing linking group were each evaluated at 1% or 2% in PP3505 polypropylene as repellent polymer melt additives. Melt-blown nonwoven webs were made according to the Melt-Blown Extrusion Procedure, and the resulting webs were evaluated for repellency using the Water Repellency Test and the Oil Repellency Test, both initially and after running the Embossing Procedure. Also, the resistance time of the nonwoven webs to dioctyl phthalate was measured using the DOP Wetting Time Test. Measurements were made initially and again after heating at 120° C. for 10 minutes. In Comparative Examples C1–C2, two fluorochemical compounds having an aliphatic moiety, an ester moiety-containing linking group but non-oligomeric (i.e., single chain) fluorochemical portion(s) were evaluated in the same fashion as an additive to PP3505 prior to extruding the nonwoven web. Both of these fluorochemicals are known in the art to be repellent ester-containing polymer melt additives and are described in World Published Patent Applications WO 97/22659 and WO 99/05345, respectively.

In Comparative Examples C3–C4, two non-oligomeric fluorochemicals known to be effective polymer melt additives were evaluated in the same fashion as an additive to PP3505 prior to extruding the nonwoven web. FX-1801 (Comp. Ex. C3) is used commercially as a polymer melt additive.

In Comparative Example C5, no polymer melt additive was incorporated into the polypropylene prior to extruding the nonwoven web.

Results are presented in TABLE 1.

meric portion containing 9 fluoroaliphatic groups (Ex. 11) was inferior in performance to its counterpart containing only 4 fluoroaliphatic groups (Ex. 10), which was unexpected considering the compound of Ex. 10 contains much less organofluorine. The combination of properties of the best performers was superior to any of the comparative materials tested which do not possess fluorochemical oligomeric portions in their structures.

Examples 20–22

Using the Contact Angle Test Procedure, advancing and receding contact angles were measured using n-hexadecane for three fluorochemical oligomeric compounds of this invention. Advancing contact angle measurement is an

TABLE 1

| Ex. | Fluorochemical Additive: Name | % | Water Rep.: Init. | Water Rep.: Annealed. | Oil Rep.: Init. | Oil Rep.: Annealed. | DOP Wet. Time |
|---|---|---|---|---|---|---|---|
| 1 | (MeFOSEA)$_4$—S—CH$_2$CH$_2$COOC$_{18}$H$_{37}$ | 1 | 3 | 8 | 0 | 1 | immed. |
| 2 | (MeFOSEA)$_4$—S—CH$_2$CH$_2$COOC$_{22}$H$_{43}$ | 1 | 3 | 9 | 0 | 1 | immed. |
| 3 | (MeFOSEA)$_4$—S—CH$_2$—CH(OOCC$_{17}$H$_{35}$)CH$_2$OOCC$_{17}$H$_{35}$ | 1 | 3 | 9 | 0 | 7 | 3 days |
| 4 | (MeFOSEA)$_4$—S—CH$_2$CH$_2$COO—UNILIN ™ 425 | 1 | 3 | 8 | 0 | 2 | 32 min. |
| 5 | (EtFOSEA)$_4$—S—CH$_2$CH$_2$COO—UNILIN ™ 425 | 1 | 4 | 9 | 0 | 2 | 10 sec. |
| 6 | (TELOMER-A)$_4$—S—CH$_2$CH$_2$COO—UNILIN ™ 425 | 1 | 5 | 10 | 0 | 3 | 4 days |
| 7 | (MeFOSEA)$_4$—S—CH$_2$CH$_2$COO—UNILIN ™ 700 | 1 | 3 | 9 | 0 | 5 | >2 days |
| 8 | (EtFOSEA)$_4$—S—CH$_2$CH$_2$COO—UNILIN ™ 700 | 1 | 3 | 9 | 0 | 5 | >2 days |
| 9 | (TELOMER-A)$_4$—S—CH$_2$CH$_2$COO—UNILIN ™ 700 | 1 | 3 | 10 | 0 | 5 | >2 days |
| 10 | (MeFOSEA)$_4$—S—CH$_2$CH$_2$OOC—UNICID ™ 700 | 1 | 3 | 9 | 0 | 5 | >2 days |
| 11 | (MeFOSEA)$_9$—S—CH$_2$CH$_2$OOC UNICID ™ 700 | 1 | 3 | 6 | 0 | 1 | 1 min. |
| 12 | (MeFOSEMA)$_4$—S—CH$_2$CH$_2$OOC—UNICID ™ 700 | 1 | 3 | 9 | 0 | 2 | >2 days |
| 13 | (MeFBSEA)$_4$—S—CH$_2$CH$_2$OOC—UNICID ™ 700 | 1 | 3 | 5 | 0 | 1 | 2 min. |
| 14 | (MeFBSEMA)$_4$—S—CH$_2$CH$_2$OOC—UNICID ™ 700 | 2 | 3 | 8.5 | 0 | 5 | 60 min |
| 15 | [(MeFOSEA)$_4$—S—CH$_2$CH$_2$COO]$_2$—PRIPOL 1070 | 1 | 3.5 | 8 | 0 | 0.5 | immed. |
| 16 | [(MeFBSEA)$_4$—S—CH$_2$CH$_2$OOC]$_2$—EMPOL ™ 1008 | 2 | 3 | 6 | 0 | 1 | 5 sec. |
| 17 | [(MeFBSEMA)$_4$—S—CH$_2$CH$_2$OOC]$_2$—EMPOL ™ 1008 | 2 | 3 | 6 | 0 | 5.5 | 10 sec. |
| 18 | (MeFOSEA)$_4$—S—CH$_2$CH$_2$COOCH$_3$ | 1 | 3 | 8 | 0 | 4 | 3.5 hr. |
| 18A | (MeFOSEA)$_4$—S—CH$_2$CH$_2$COO—UNITHOX ™ 750 | 1 | 3 | 7 | 0 | 5 | NOT RUN |
| 19 | (MeFOSEA)$_4$—S—CH$_2$CH$_2$COOCH$_2$CH$_2$N(CH$_3$)SO$_2$C$_8$F$_{17}$ | 1 | 3 | 7 | 0 | 3 | 2 min. |
| C1 | C$_8$F$_{17}$SO$_2$N(CH$_3$)CH$_2$CH$_2$OOC—UNICID ™ 700 | 1 | 4.5 | 5 | 0 | 0 | 10 sec. |
| C2 | [C$_8$F$_{17}$SO$_2$N(CH$_3$)CH$_2$CH$_2$OOC]$_2$—EMPOL ™ 1008 | 1 | 7 | 9 | 1 | 2 | immed. |
| C3 | FC Oxazolidinone A | 1 | 9 | 9 | 2 | 2 | >2 days |
| C4 | FC Oxazolidinone B | 1 | 3 | 7 | 0 | 0 | >2 days |
| C5 | No Additive | — | 2 | 2 | 0 | 0 | immed. |

The data in TABLE 1 show that the compounds of the invention which have fluorochemical oligomeric portions, an aliphatic moiety and a ester moiety-containing linking group generally exhibited good to excellent water and oil resistance after embossing. Additionally, they exhibited good to excellent resistance to penetration by DOP. The good repellency to oils and DOP is surprising, considering the size of the oleophilic hydrocarbon groups attached to the compounds (except for Ex. 18). The fluorochemical oligoexcellent predictor for water and oil repellency, and receding contact angle is an excellent predictor for soil resistance. Thus, any compound exhibiting high advancing and receding contact angles would be expected to be an excellent candidate as a textile, leather or carpet treatment.

Results are presented in TABLE 2.

TABLE 2

| Ex. | Fluorochemical Additive | Adv. Contact Angle: Water | Adv. Contact Angle: n-$C_{16}H_{34}$ | Rec. Contact Angle: Water | Rec. Contact Angle: n-$C_{16}H_{34}$ |
|---|---|---|---|---|---|
| 20 | (MeFOSEA)$_4$—S—CH$_2$CH$_2$COOC$_{18}$H$_{37}$ | 98.8 | 76.3 | 71.9 | 55.3 |
| 21 | (MeFOSEA)$_4$—S—CH$_2$CH$_2$COOC$_{22}$H$_{43}$ | 99.1 | 77.9 | 69.1 | 56.7 |
| 22 | (MeFOSEA)$_4$—S—CH$_2$CH$_2$COO-UNILIN ™ 700 | 99.1 | 77.5 | 68.0 | 59.6 |

The data in TABLE 2 show that all three compounds exhibited very good advancing and receding contact angles. Surprisingly, even the compound with the very long alkyl group (i.e., derived from UNILIN™ 700) demonstrated excellent contact angles against n-hexadecane.

Example 23–25 and Comparative Examples C6–C8

In Examples 23–25, three fluorochemical oligomeric compounds of this invention were incorporated at 1% into polypropylene and films were made using the Film Extrusion Procedure. Each film was then evaluated for release using the Peel Force Test Procedure, both initially and after aging for 2 days at 49° C. (120° F.). The release properties were compared to the properties imparted to the polypropylene by two known fluorochemical polymer melt additives (Comp. Ex. C6–C7) and when no polymer melt additive was employed (Comp. Ex. C8).

Results are presented in TABLE 3.

TABLE 3

| Ex. | Fluorochemical Additive | Peel Force, oz/in (N/m): Init. | Peel Force, oz/in (N/m): Aged |
|---|---|---|---|
| 23 | (MeFOSEA)$_4$—S—CH$_2$CH$_2$COOC$_{18}$H$_{37}$ | 5.2 | 12 |
| 24 | (MeFOSEA)$_4$—S—CH$_2$CH$_2$COO-UNLIN ™ 425 | 1.1 | 17 |
| 25 | (MeFOSEA)$_4$—S—CH$_2$CH$_2$COO-UNLIN ™ 700 | 1.5 | 16 |
| C6 | FC Oxazolidinone A | 6.9 | 36 |
| C7 | [C$_8$F$_{17}$SO$_2$N(CH$_3$)CH$_2$CH$_2$OOC]$_2$—EMPOL ™ 1008 | 14 | 33 |
| C8 | None | 6.9 | 25 |

The data in TABLE 3 demonstrate that the three fluorochemical oligomeric compounds clearly outperform the other two fluorochemical polymer melt additives in imparting release properties to polypropylene.

Examples 26–27 and Comparative Examples C9–C10

Fluorochemical oligomeric compounds were added to two different thermoplastic resins, a polyethylene (PE6806) and a polyurethane (PS440–200), webs were made according to the Melt-Blown Extrusion Procedure, and the resulting webs were evaluated for repellency using the Water Repellency Test and the Oil Repellency Test, The melt-blown fabric were tested initially and after annealing at 120° C. for 10 minutes. Also, the DOP Wetting Time Test was run on the nonwoven webs.

Results from these evaluations are presented in TABLE 4.

TABLE 4

| Ex. | Polymer | Fluorochemical Additive | Water Rep.: Init. | Water Rep.: Annealed. | Oil Rep.: Init. | Oil Rep.: Annealed. | DOP Wet. Time |
|---|---|---|---|---|---|---|---|
| 26 | PE6806 | (MeFOSEA)$_4$—S—CH$_2$CH$_2$COO—UNILIN ™ 700 | 3 | 10 | 0 | 6 | >2 days |
| C9 | PE6806 | None | 2 | 2 | 0 | 0 | immed. |
| 27 | PS440-200 | (TELOMER-A)$_4$—S—CH$_2$CH$_2$COO—UNILIN ™ 700 | 4 | 8 | 5 | 7 | 3.5 hr. |
| C10 | PS440-200 | None | 2 | 3 | 0 | 0 | immed. |

The data in TABLE 4 show that incorporation of the fluorochemical oligomeric compounds into either the polyethylene or the polyurethane resin greatly enhanced water and oil resistance, immediately and/or after annealing. Also, the DOP holdout imparted by each of the fluorochemical oligomeric compounds was excellent.

Example 28 and Comparative Example C11

Molded castings were made from a two-part, room temperature-curable, thermoset epoxy resin system (3M Scotch-Weld™ 2158 B/A Epoxy Adhesive Tube Kit) with and without (MeFOSEA)$_4$—S—CH$_2$CH$_2$OOC-UNICID™ 700, an alkylated fluorochemical oligomeric compound of this invention. After curing, the castings were evaluated for water and oil repellency.

In Example 28, 4.9 g of Part A, 4.9 g of Part B and 0.20 g of (MeFOSEA)$_4$—S—CH$_2$CH$_2$OOC-UNICID™ 700 were mixed together in an approximately 60 mm diameter aluminum weighing pan. The sample was cured for 1 hour at 80° C. and was left overnight at room temperature. The Water Repellency Test and the Oil Repellency Test were then run on the surface of the cured casting; the same test liquids and rating scale were used as with the nonwoven web repellency test, with the reported value corresponding to the highest number test liquid for which a drop, when placed on the surface of the film, would not spread.

In Comparative Example C11, the same epoxy resin preparation and evaluation was run as described in Example 28, except that the (MeFOSEA)$_4$—S—CH$_2$CH$_2$OOC-UNICID™ was omitted. Results are presented in TABLE 5.

TABLE 5

| Ex. | Composition of Epoxy Casting | Water Repellency | Oil Repellency |
|---|---|---|---|
| 28 | 2158 + 2% (MeFOSEA)$_4$-S—CH$_2$CH$_2$OOC-UNICID ™ 700 | 9 | 7 |
| C11 | 2158 only | 1.5 | 0 |

The data in TABLE 5 show that the casting made from epoxy resin having alkylated fluorochemical oligomeric compound added thereto exhibited dramatically improved water and oil repellency relative to the casting made from epoxy resin only.

Examples 29–30 and Comparative Examples C12–C13

Molded castings were made from a one-part, moisture-curable, thermoset polyurethane resin system (3M EC-5200 Marine Adhesive Sealant) with and without (MeFOSEA)$_4$—S—CH$_2$CH$_2$OOC-UNICID™ 700, an alkylated fluorochemical oligomeric compound of this invention. After curing, the castings were evaluated for water and oil repellency.

For each example, 4.9 g of EC-5200 sealant and 0.1 g of (MeFOSEA)$_4$—S—CH$_2$CH$_2$OOC-UNICID™ 700 were mixed together in two approximately 60 mm diameter aluminum weighing pans, and the mixture was heated with a heat gun and stirred until a homogeneous mixture resulted. For Example 29, the resin system in the first pan was allowed to cure for 63 hours under ambient conditions (roughly 50% relative humidity). For Example 30, the resin system in the second pan was baked for 63 hours at 50° C. above a pan of water. The Water Repellency Test and the Oil Repellency Test were then run on the surface of each cured resin; the same test liquids and rating scale were used as with the nonwoven web repellency test, with the reported value corresponding to the highest number test liquid for which a drop, when placed on the surface of the film, would not spread.

In Comparative Examples C12–C13, the same moisture-cured polyurethane resin preparation and evaluation was run as described in Examples 29 and 30, respectively, except that the (MeFOSEA)$_4$—S—CH$_2$CH$_2$OOC-UNICID™ 700 was omitted.

Results are presented in TABLE 6.

TABLE 6

| Ex. | Composition of Urethane Casting | Ambient or Bake | Water Repel. | Oil Repel. |
|---|---|---|---|---|
| 29 | EC-5200 + 2.0% (MeFOSEA)$_4$—S—CH$_2$CH$_2$OOC-UNICID ™ 700 | Ambient | 10 | 8 |
| C12 | EC-5200 only | Ambient | 2 | 0 |
| 30 | EC-5200 + 2.0% (MeFOSEA)$_4$—S—CH$_2$CH$_2$OOC-UNICID ™ 700 | Bake | 10 | 8 |
| C13 | EC-5200 only | Bake | 7 | 1 |

The data in TABLE 6 show that the casting made from moisture-cured polyurethane resin having (MeFOSEA)$_4$—S—CH$_2$CH$_2$OOC-UNICID™ 700 added thereto exhibited dramatically improved water and oil repellency to the casting made from moisture-cured polyurethane resin only, cured either under ambient conditions or baked.

Example 31–33 and Comparative Examples C14–C16

Using the Film Extrusion Procedure, films with an average thickness of approximately 7 mils (0.3 mm) were cast from PP3545 polypropylene, with and without 3% polymer melt additive. Three fluorochemical oligomeric compounds of this invention were evaluated, along with two fluorochemical polymer melt additives known in the art. The resulting films were evaluated for repellency using the Water Repellency Test and the Oil Repellency Test. Results are presented in TABLE 7.

TABLE 7

| Ex. | Fluorochemical Additive | Water Repellency | Oil Repellency |
|---|---|---|---|
| 31 | (MeFOSEA)$_4$-S—CH$_2$CH$_2$COO—C$_{18}$H$_{37}$ | 10 | 4.5 |
| 32 | (MeFOSEA)$_4$-S—CH$_2$CH$_2$COO—C$_{22}$H$_{45}$ | 9 | 7 |
| 33 | (MeFOSEA)$_4$-S—CH$_2$CH$_2$COO-UNILIN ™ 700 | 10 | 7 |
| C14 | FC Oxazolidinone A | 10 | 7 |
| C15 | [C$_8$F$_{17}$SO$_2$N(CH$_3$)CH$_2$CH$_2$OOC]$_2$-EMPOL ™ 1008 | 9 | 2 |
| C16 | — | 2 | 0 |

The data in TABLE 7 show that the films containing the fluorochemical oligomeric compounds were comparable or superior in repellency to the films containing the state-of-the-art fluorochemical polymer melt additives.

Examples 34–38 and Comparative Examples C17–C19

This series of experiments was run to show the utility of fluorochemical oligomeric compounds of this invention as polymer melt additives for oily mist resistant electret filter media which are treated by corona discharge.

In Comparative Example C17, PP3505 polypropylene with no polymer melt additive was extruded as described in the Melt-Blown Extrusion Procedure at a melt temperature of 297° C. to form melt blown microfiber web having a basis weight of 54 g/m$^2$ and a thickness of 0.79 mm. The fibers in the web had an average effective fiber diameter of 8.0±1.0 μm. The web was annealed at 149° C. for 5 minutes and then corona charged using a high voltage electric field provided between a corona source and a ground electrode with a corona current of about 0.01 milliamp per centimeter of corona source.

In Examples 34–38, nonwoven webs were prepared according to the procedure of Comparative Example C17, except this time fluorochemical compounds of this invention were added at about 1.1% to the PP3505 polypropylene prior to extrusion. In Comparative Examples C18–C19, nonwoven webs were prepared according to the procedure of Comparative Example C17, except this time polymer melt additives known in the art were added at about 1.1% to the PP3505 polypropylene prior to extrusion.

The % DOP penetration (% Pn), the pressure drop (ΔP) and the quality factor (QF) were determined for each sample using the DOP Penetration and Pressure Drop Test. Results are presented in TABLE 8.

TABLE 8

| Ex. | Fluorochemical Additive | % Pn | ΔP (mm of water) | QF 1/(mm of water) |
|---|---|---|---|---|
| C17 | — | 28.4 | 2.46 | 0.512 |
| 34 | (TELOMER-A)$_4$-S—CH$_2$CH$_2$COO-UNILIN ™ 700 | 26.2 | 2.75 | 0.487 |
| 35 | (MeFOSEA)$_4$-S—CH$_2$CH$_2$COO-UNILIN ™ 700 | 19.4 | 3.08 | 0.532 |
| 36 | (MeFOSEA)$_4$-S—CH$_2$CH$_2$COO-C$_{18}$H$_{37}$ | 16.5 | 2.19 | 0.823 |
| 37 | (MeFOSEA)$_4$-S—CH$_2$CH$_2$OOC-UNICID ™ 700 | 25.9 | 1.89 | 0.715 |
| 38 | (MeFOSEA)$_4$-S—CH$_2$CH$_2$COO-CH$_2$CH$_2$N(CH$_3$)SO$_2$C$_8$F$_{17}$ | 23.6 | 1.87 | 0.772 |
| C18 | FC Oxazolidinone A | 22.4 | 2.13 | 0.723 |
| C19 | [C$_8$F$_{17}$SO$_2$N(CH$_3$)CH$_2$CH$_2$OOC]$_2$-EMPOL ™ 1008 | 27.1 | 2.56 | 0.510 |

The data in TABLE 8 show that improved overall performance is realized when certain fluorochemical oligomeric compounds are employed as compared to the comparative polymer melt additives or no melt additive at all.

Examples 39–43 and Comparative Examples C20–C22

This series of experiments was run to show the utility of fluorochemical oligomeric compounds of this invention as polymer melt additives for oily mist resistant electret filter media charged using jets of water.

In Comparative Example C20, PP3505 polypropylene with no polymer melt additive was extruded as described in the Melt-Blown Extrusion Procedure at a melt temperature of 297° C. to form melt blown microfiber web having a basis weight of 54 g/m$^2$ and a thickness of 0.79 mm. The fibers in the web had an average effective fiber diameter of 8.0±1.0 μm. The web was annealed at 149° C. for 5 minutes. Hydrocharging was performed by passing the web sample at a rate of 5 cm/second across a vacuum slot 25.4 cm long and 0.5 cm wide powered by a Dayton 2Z974B™ vacuum cleaner (Dayton Electric, Chicago). A pair of Spraying Systems Teejet 9501™ sprayer nozzles was mounted 10 cm apart and centered 7 cm above the vacuum slot. Deionized water was sprayed through the nozzles with a hydrostatic pressure of about 90 psi (620 kPa). The web is passed through the spray on one side then inverted and passed through a second time such that both sides of the web were sprayed. The spray was turned off and the web passed across a vacuum slot with no water spray such that each side is exposed to the vacuum to remove excess water. The web was then hung to dry at ambient conditions.

In Examples 39–43, nonwoven webs were prepared according to the procedure of Comparative Example C20, except this time fluorochemical compounds of this invention were added at about 1.1% to the PP3505 polypropylene prior to extrusion. In Comparative Examples C21–C22, nonwoven webs were prepared according to the procedure of Comparative Example C20, except this time polymer melt additives known in the art were added at about 1.1% to the PP3505 polypropylene prior to extrusion.

The % DOP penetration (% Pn), the pressure drop (ΔP) and the quality factor (QF) were determined for each sample using the DOP Penetration and Pressure Drop Test. Results are presented in TABLE 9.

TABLE 9

| Ex. | Fluorochemical Additive | % Pn | ΔP | QF |
|---|---|---|---|---|
| C20 | — | 12.2 | 2.31 | 0.911 |
| 39 | (TELOMER-A)$_4$-S—CH$_2$CH$_2$COO-UNILIN ™ 700 | 3.30 | 2.85 | 1.197 |
| 40 | (MeFOSEA)$_4$-S—CH$_2$CH$_2$COO-UNILIN ™ 700 | 1.60 | 3.31 | 1.249 |
| 41 | (MeFOSEA)$_4$-S—CH$_2$CH$_2$COO-C$_{18}$H$_{37}$ | 7.24 | 1.97 | 1.333 |
| 42 | (MeFOSEA)$_4$-S—CH$_2$CH$_2$OOC-UNICID ™ 700 | 6.40 | 1.84 | 1.494 |
| 43 | (MeFOSEA)$_4$-S—CH$_2$CH$_2$COO-CH$_2$CH$_2$N(CH$_3$)SO$_2$C$_8$F$_{17}$ | 11.00 | 1.77 | 1.247 |
| C21 | FC Oxazolidinone A | 3.98 | 2.27 | 1.472 |
| C22 | [C$_8$F$_{17}$SO$_2$N(CH$_3$)CH$_2$CH$_2$OOC]$_2$-EMPOL ™ 1008 | 9.90 | 2.96 | 0.781 |

The data in TABLE 9 show the fluorochemical oligomeric compounds of this invention generally perform well in this application. Generally Quality Factors (QF), for flat media, in excess of 0.3 cannot be achieved in any way except through electret enhancement.

We claim:

1. Fluorochemical oligomeric compounds of the formula:

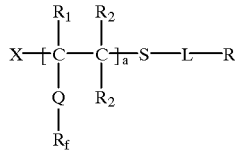

wherein each L independently comprises a linking group;

R is a linear, monovalent alkyl group of 12 to 75 carbon atoms;

a is an integer such that A is oligomeric and comprises a plurality of $R_f$ groups;

each $R_1$ is independently a hydrogen, halogen, or straight chain or branched chain alkyl containing 1 to about 4 carbon atoms;

each $R_2$ is independently hydrogen or straight chain or branched chain alkyl containing 1 to about 4 carbon atoms;

each Q is a covalent bond or an organic linking group;

$R_f$ is a fluoroaliphatic group;

X is a hydrogen atom or a group derived from a free radical initiator.

2. The compounds of claim 1 wherein a is 3 to 8.

3. The compounds of claim 2 wherein $R_f$ has the structure $C_oF_{2o+1}$, where o is 4 to 14.

4. The compounds of claim 1 wherein L is selected from the group of a covalent bond, straight chain, branched chain, or cyclic alkylene, arylene, aralkylene, oxy, oxo, hydroxy, thio, sulfonyl, sulfoxy, amino, imino, sulfonamido, carboxamido, carbonyloxy, urethanylene, ureylene, and combinations thereof.

5. The compounds of claim 4 wherein L is chosen from the group consisting of

| | |
|---|---|
| —(CH$_2$)$_k$O(O)C— | —CH$_2$CH(OR$_2$')CH$_2$C(O)O— |
| —(CH$_2$)$_k$C(O)O— | —(CH$_2$)$_k$O— and |
| —(CH$_2$)$_k$O(CH$_2$)$_k$O(O)C— | | wherein each k is independently an integer from 0 to about 20, and R$_2$' is alkyl of 1 to about 20 carbon atoms.

6. The compounds of claim 2 comprising oligomerized units of compounds of the formula

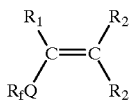

wherein R$_1$, R$_2$, R$_f$ and Q are as defined in claim 2.

7. A synthetic organic polymer composition comprising one or more compounds of claim 2 and a synthetic organic polymer.

8. The polymer composition of claim 7 wherein the synthetic organic polymer is a thermoplastic polymer.

9. The composition of claim 8 wherein said thermoplastic polymers are selected from the group consisting of polyamides, polyesters, polyurethanes, and polyolefins.

10. The composition of claim 7 wherein said compounds comprises from 0.5 to 5 weight percent of said composition.

11. A shaped article comprising a melt-processible thermoplastic polymer and the compounds of claim 1.

12. The shaped article of claim 11 wherein said compounds provide from 100 to 10,000 ppm fluorine.

13. The shaped article of claim 11 selected from the group of films, sheets and fibers.

14. An oily mist resistant electret filter medium comprising polypropylene electret fibers and the compounds of claim 1.

15. The filter medium of claim 14 wherein said fibers have an effective fiber diameter of 2 to 30 micrometers.

16. The filter medium of claim 14 wherein said fibers have been annealed.

17. The filter medium of claim 14 wherein said filter media has a basis weight of 10 to 100 g/m$^2$.

18. The compounds of claim 1 wherein Q is selected from the group consisting of

| | |
|---|---|
| —SO$_2$NR$_1$'(CH$_2$)$_k$O(O)C— | —CONR$_1$'(CH$_2$)$_k$O(O)C— |
| —(CH$_2$)$_k$O(O)C— | —CH$_2$CH(OR$_2$')CH$_2$O(O)C— |
| —(CH$_2$)$_k$C(O)O— | —(CH$_2$)$_k$SC(O)— |
| —(CH$_2$)$_k$O(CH$_2$)$_k$O(O)C— | —(CH$_2$)$_k$S(CH$_2$)$_k$O(O)C— |
| —(CH$_2$)$_k$SO2(CH$_2$)$_k$O(O)C— | |
| —(CH$_2$)$_k$SO$_2$NR$_1$'(CH$_2$)$_k$O(O)C— | —(CH$_2$)$_k$SO$_2$— |
| —SO$_2$NR$_1$'(CH$_2$)$_k$O— | —SO$_2$NR$_1$'(CH$_2$)$_k$— |
| —(CH$_2$)$_k$O(CH$_2$)$_k$C(O)O— | —(CH$_2$)$_k$SO$_2$NR$_1$'(CH$_2$)$_k$C(O)O— |
| —(CH$_2$)$_k$SO$_2$(CH$_2$)$_k$C(O)O— | —CONR$_1$'(CH$_2$)$_k$C(O)O— |
| —(CH$_2$)$_k$S(CH$_2$)$_k$C(O)O— | —CH$_2$CH(OR$_2$')CH$_2$C(O)O— |
| —SO$_2$NR$_1$'(CH$_2$)$_k$C(O)O— and | —(CH$_2$)$_k$C— | wherein each k is independently an integer from 0 to about 20, R$_1$' is hydrogen, phenyl, or alkyl of 1 to about 4 carbon atoms, and R$_2$' is alkyl of 1 to about 20 carbon atoms.

19. The composition of claim 7 wherein the synthetic organic polymer is a thermoset polymer.

20. The composition of claim 19 wherein said thermoset polymer is selected from the group consisting of epoxy resins, urethanes and acrylates.

21. The compounds of claim 1 wherein R is an alkyl group of 18 to 60 carbon atoms, a version marked up to show changes made to the claim(s) relative to the previous version of the claim(s) is attached.

* * * * *

UNITED STATES PATENT AND TRADEMARK OFFICE
CERTIFICATE OF CORRECTION

PATENT NO. : 6,288,157 B1
DATED : September 11, 2001
INVENTOR(S) : Jariwala, Chetan P.

It is certified that error appears in the above-identified patent and that said Letters Patent is hereby corrected as shown below:

Column 16,
Line 9, delete "equi molar" and insert in place thereof -- -- equimolar --.

Column 17,
Line 41, delete "$C_8$" and insert in place thereof -- $C_{18}$ --.

Column 18,
Lines 44-45, delete "$CH_2$" and insert in place thereof -- $CH_2CH_2$. --.
Liune 54, delete "H" and insert in place thereof -- OH --.

Column 23,
Table 1, Ex. 11, between "C" and "U" add -- — --.

Column 25,
Table 3, Ex. 24, delete "UNLIN$^{TM}$" and insert in place thereof -- UNILIN$^{TM}$ --.
Table 3, Ex. 25, delete "UNLIN$^{TM}$" and insert in place thereof -- UNILIN$^{TM}$ --.

Column 32,
Line 14, delete "2" and insert in place thereof -- $_2$ --.
Line 33, delete "a version marked up to show changes made to the claim(s) relative to the previous version of the claim(s) is attached."

Signed and Sealed this

Fourteenth Day of September, 2004

JON W. DUDAS
*Director of the United States Patent and Trademark Office*